United States Patent [19]
Cocuzza et al.

[11] Patent Number: 6,103,737
[45] Date of Patent: Aug. 15, 2000

[54] ARYL- AND ARYLAMINO- SUBSTITUTED HETEROCYCLES AS CORTICOTROPIN RELEASING HORMONE ANTAGONISTS

[75] Inventors: Anthony J. Cocuzza; Frank W. Hobbs, both of Wilmington; James P. Beck, Smyrna; Paul J. Gilligan, Wilmington, all of Del.

[73] Assignee: DuPont Pharmaceuticals Company, Wilmington, Del.

[21] Appl. No.: 09/109,395

[22] Filed: Jul. 2, 1998

Related U.S. Application Data

[60] Provisional application No. 60/051,745, Jul. 3, 1997.

[51] Int. Cl.[7] .................................................. A61K 31/47
[52] U.S. Cl. ...................... 514/310; 514/810; 514/885; 514/886; 514/909; 514/925
[58] Field of Search ..................................... 514/310, 810, 514/885, 886, 909, 925

[56] References Cited

FOREIGN PATENT DOCUMENTS

96/05177  2/1996  WIPO .

OTHER PUBLICATIONS

Petel, Journal of Geriatric Psychiatry and Neurology, vol. 8, 81–95, (1995).
Ehlert et al., Life Sciences, vol. 55, No. 25/26, 2135–2145, (1994).

*Primary Examiner*—Howard C. Lee
*Assistant Examiner*—Everett White
*Attorney, Agent, or Firm*—Maureen P. O'Brien; Kenneth B. Rubin

[57] ABSTRACT

Corticotropin releasing factor (CRF) antagonists of formula I:

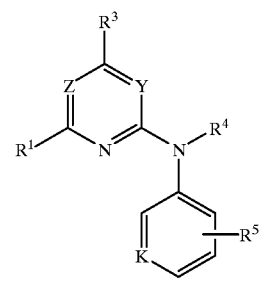

and their use in treating psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

7 Claims, No Drawings

ARYL- AND ARYLAMINO- SUBSTITUTED HETEROCYCLES AS CORTICOTROPIN RELEASING HORMONE ANTAGONISTS

This application claims the benefit of U.S. Provisional Application No. 60/051,745, filed Jul. 3, 1997.

FIELD OF THE INVENTION

The present invention relates to novel compounds, compositions, and methods for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. In particular, the present invention relates to certain arylamino-substituted pyrimidines and triazines or certain aryl-substituted azolopyridines and pyrimidines, pharmaceutical compositions containing such compounds and their use in treating psychiatric disorders, neurological diseases, immunological, cardiovascular or heart-related diseases and colonic hypersensitivity associated with psychopathological disturbance and stress

BACKGROUND OF THE INVENTION

Corticotropin releasing factor (herein referred to as CRF), a 41 amino acid peptide, is the primary physiological regulator of proopiomelanocortin(POMC)—derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

It has been further postulated that CRF has a role in immunological, cardiovascular or heart-related diseases such as hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

Aldrich et al. (DuPont Merck) PCT Application US94/11050 describes a broad class of CRF antagonist compounds, including compounds which can be represented by the formula:

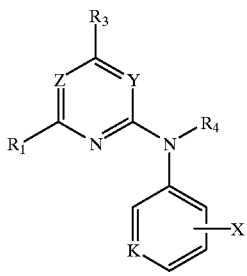

wherein $R^3$ can be phenyl, biphenyl, napthyl, pyridinyl, 2-methyl-3-pyridinyl, 4-methyl-3-pyridinyl, or pyrimidinyl and R1, R2, R4, K and X can have some of the same meanings as in this invention. The compounds of this invention do not include unsubstituted phenyl, biphenyl, napthyl, pyridinyl, or pyrimidinyl or 2-methyl-3-pyridinyl or 4-methyl-3-pyridinyl at the $R^3$ position.

Other compounds reported to have activity as corticotropin releasing factors are disclosed in WO 94/13676 and WO 94/13643.

SUMMARY OF THE INVENTION

In accordance with one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

According to another aspect, the present invention provides novel compounds of formula (I) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of formula (I), and methods of using such compounds for the suppression of CRF hypersecretion, and/or for the treatment of anxiogenic disorders.

According to yet another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in mammals.

According to a still further aspect of the invention, the compounds provided by this invention (and especially labeled compounds of this invention) are also useful as standards and reagents in determining the ability of a potential pharmaceutical to bind to the CRF receptor.

DETAILED DESCRIPTION OF THE INVENTION

[1] Thus, in a first embodiment, the present invention provides a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals, comprising: administering to the mammal a therapeutically effective amount of a compound of formula (I):

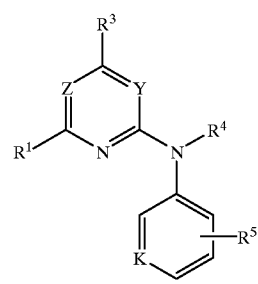

(I)

or a stereoisomer or pharmaceutically acceptable salt form thereof, wherein:
Y is $CR^2$ or N;
Z is CH or N;
K is $CR^5$ or N;

$R^1$ is $C_1$–$C_4$ alkyl, $C_2$–$C_4$ alkenyl, $C_2$–$C_4$ alkynyl, chloro, fluoro, cyano, or trifluoromethyl;

$R^2$ taken together with $R^4$ is —E—F—, where E and F are independently $CR^9$ and $CR^{9a}$; or $R^2$ taken together with $R^4$ is —A═D—, where A and D are each independently CH, $CR^{10}$ or N; provided that —A═D— may not be —CH═N— or $CR^{10}$═N— oriented in such a way as to form a pyrazole ring, but may be —CH═N— or $CR^{10}$═N— oriented in such a way as to form an imidazole ring; or $R^2$ taken together with $R^4$ is —A—D— where A is $NR^9$ and D is C═O oriented in such a way as to form an imidazolone.

$R^3$ is phenyl substituted on 1–4 ring carbons with $R^8$, napthyl substituted on 1–4 ring carbons with $R^8$, pyridinyl substituted on 1–4 ring carbons with $R^8$, or pyrimidinyl substituted on 1–3 ring carbons with $R^8$;

$R^4$ is $C_1$–$C_4$ alkyl, allyl, or propargyl, where $C_1$–$C_4$ alkyl is optionally substituted with $C_3$–$C_6$ cycloalkyl, OH, —$OR^9$, —$S(O)_nR^9$ or —$CO_2R^9$;

$R^5$ represents 1–4 substituents on ring carbons each of which may be independently $C_1$–$C_{10}$ alkyl, $C_2$–$C_{10}$ alkenyl, $C_2$–$C_{10}$ alkynyl, $C_3$–$C_6$ cycloalkyl, $C_4$–$C_{10}$ cycloalkylalkyl, halo, nitro, cyano, —$NR^6R^7$, —$OR^7$, —$COR^7$, —$C(O)NR^6R^7$, —$C(NOR^9)R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{10}$ cycloalkylalkyl are optionally substituted with 1 to 3 substituents independently selected from halo, nitro, cyano, —$NR^6R^7$, —$OR^7$, —$COR^7$, —$C(O)NR^6R^7$, —$S(O)_nR^7$, and —$C(NOR^9)R^7$ and two $R^5$ moieties taken together may comprise $CR^9R^{9a}CR^9R^{9a}O$, $CR^9R^{9a}CR^9R^{9a}CR^9R^{9a}$, or $CR^9$═$CR^{9a}O$;

$R^6$ and R7 are independently at each occurrence H, $C_1$–$C_6$ alkyl, $C_3$–$C_6$ cycloalkyl, —$(CH_2)_m$-phenyl, or —$(CH_2)_m$-heteroaryl; all optionally substituted with 1–3 $R^{11}$'s.

$R^8$ is independently at each occurrence $C_1$–$C_6$ alkyl, $C_2$–$C_6$ alkenyl, $C_2$–$C_6$ alkynyl, $C_3$–$C_6$ cycloalkyl, $C_4$–$C_{10}$ cycloalkylalkyl, phenyl, heteroaryl, halo, nitro, cyano, —$NR^6R^7$, —$OR^7$, —$COR^7$, —$C_2R^7$, —$C(O)NR^6R^7$, —$OC(O)NR^6R^7$, —$NR^9C(O)NR^6R^7$, —$NR^6C(O)R^7$, —$C(NOR^9)R^7$, —$S(O)_nR^7$, —$NR^9SO_2R^7$, —$SO_2NR^6R^7$, and where $C_1$–$C_6$ alkyl, $C_2$–$C_6$ alkenyl, $C_2$–$C_6$ alkynyl, $C_3$–$C_6$ cycloalkyl, $C_4$–$C_{10}$ cycloalkylalkyl, and phenyl are optionally substituted with 1 to 3 substituents independently selected from halo, nitro, cyano, —$NR^6R^7$, —$OR^7$, —$COR^7$, —$C(O)NR^6R^7$, —$S(O)_nR^7$, —$C(NOR^9)R^7$, —$NR^9SO_2R^7$, and —$SO_2NR^6R^7$; provided that when $R^3$ is pyridinyl, at least one $R^8$ is other than methyl; further provided that when $R^3$ is phenyl, at least one $R^8$ is other than unsubstituted phenyl;

$R^9$ and $R^{9a}$ is H or $C_1$–$C_4$ alkyl;

$R^{10}$ is $C_1$–$C_4$ alkyl, halo, nitro, cyano, —$NR^9R^{9a}$, —$OR^{12}$, or —$S(O)_nR^{12}$;

$R^{11}$ is independently at each occurrence $C_1$–$C_3$ alkyl, halo, nitro, cyano, —$NR^9R^{9a}$, —$OR^9$ —$S(O)_nR^{12}$, —$COR^9$, —$CO_2R^9$, —$C(O)NR^9R^{9a}$, —$NR^9C(O)R^{9a}$, or —$C(NOR^9)R^{9a}$.

$R^{12}$ is $C_1$–$C_4$ alkyl;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl, 2,3-dihydrobenzofuranyl or 2,3-dihydrobenzothienyl;

n is independently at each occurrence 0, 1 or 2; and
m is independently at each occurrence 0–6.

[2] In a preferred embodiment, the present invention provides a novel compound of formula I:

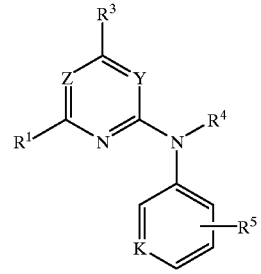

(I)

or a stereoisomer or pharmaceutically acceptable salt form thereof, wherein:

Y is $CR^2$ or N;

Z is CH or N;

K is $CR^5$ or N;

$R^1$ is $C_1$–$C_4$ alkyl, $C_2$–$C_4$ alkenyl, $C_2$–$C_4$ alkynyl, chloro, fluoro, cyano, or trifluoromethyl;

$R^2$ taken together with $R^4$ is —E—F—, where E and F are independently $CR^9$ and $CR^{9a}$; or $R^2$ taken together with $R^4$ is —A═D—, where A and D are each independently CH, $CR^{10}$ or N; provided that —A═D— may not be —CH═N— or $CR^{10}$═N— oriented in such a way as to form a pyrazole ring, but may be —CH═N— or $CR^{10}$═N— oriented in such a way as to form an imidazole ring; or $R^2$ taken together with $R^4$ is —A—D— where A is $NR^9$ and D is C═O oriented in such a way as to form an imidazolone.

$R^3$ is phenyl substituted on 1–4 ring carbons with $R^8$, napthyl substituted on 1–4 ring carbons with $R^8$, pyridinyl substituted on 1–4 ring carbons with $R^8$, or pyrimidinyl substituted on 1–3 ring carbons with $R^8$;

$R^4$ is $C_1$–$C_4$ alkyl, allyl, or propargyl, where $C_1$–$C_4$ alkyl is optionally substituted with $C_3$–$C_6$ cycloalkyl, OH, —$OR^9$, —$S(O)_nR^9$ or —$CO_2R^9$;

$R^5$ represents 1–4 substituents on ring carbons each of which may be independently $C_1$–$C_{10}$ alkyl, $C_2$–$C_{10}$ alkenyl, $C_2$–$C_{10}$ alkynyl, $C_3$–$C_6$ cycloalkyl, $C_4$–$C_{10}$ cycloalkylalkyl, halo, nitro, cyano, —$NR^6R^7$, —$OR^7$, —$COR^7$, —$C(O)NR^6R^7$, —$C(NOR^9)R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{10}$ cycloalkylalkyl are optionally substituted with 1 to 3 substituents independently selected from halo, nitro, cyano, —$NR^6R^7$, —$OR^7$, —$COR^7$, —$C(O)NR^6R^7$, —$S(O)_nR^7$, and —$C(NOR^9)R^7$ and two $R^5$ moieties taken together may comprise $CR^9R^{9a}CR^9R^9O$, $CR^9R^{9a}CR^9R^{9a}CR^9R^{9a}$, or $CR^9$═$CR^{9a}O$;

$R^6$ and R7 are independently at each occurrence H, $C_1$–$C_6$ alkyl, $C_3$–$C_6$ cycloalkyl, —$(CH_2)_m$-phenyl, or —$(CH_2)_m$-heteroaryl; all optionally substituted with 1–3 $R^{11}$'s.

$R^8$ is independently at each occurrence $C_1$–$C_6$ alkyl, $C_2$–$C_6$ alkenyl, $C_2$–$C_6$ alkynyl, $C_3$–$C_6$ cycloalkyl, $C_4$–$C_{10}$ cycloalkylalkyl, phenyl, heteroaryl, halo, nitro, cyano, —$NR^6R^7$, —$OR^7$, —$COR^7$, —$CO_2R^7$, —$C(O)NR^6R^7$, —$OC(O)NR^6R^7$, —$NR^9C(O)NR^6R^7$, —$NR^6C(O)R^7$, —$C(NOR^9)R^7$, —$S(O)_nR^7$, —$NR^9SO_2R^7$, —$SO_2NR^6R^7$, and where $C_1$–$C_6$ alkyl, $C_2-C_6$ alkenyl, $C_2-C_6$ alkynyl, $C_3-C_6$ cycloalkyl, $C_4-C_{10}$ cycloalkylalkyl, and phenyl are optionally substituted with 1 to 3 substituents independently selected from halo, nitro, cyano, $-NR^6R^7$, $-OR^7$, $-COR^7$, $-C(O)NR^6R^7$, $-S(O)_nR^7$, $-C(NOR^9)R^7$, $-NR^9SO_2R^7$, and $-SO_2NR^6R^7$; provided that when $R^3$ is pyridinyl, at least one $R^8$ is other than methyl; further provided that when $R^3$ is phenyl, at least one $R^8$ is other than unsubstituted phenyl;

$R^9$ and $R^{9a}$ is H or $C_1-C_4$ alkyl;

$R^{10}$ is $C_1-C_4$ alkyl, halo, nitro, cyano, $-NR^9R^{9a}$, $-OR^{12}$, or $-S(O)_nR^{12}$;

$R^{11}$ is independently at each occurrence $C_1-C_3$ alkyl, halo, nitro, cyano, $-NR^9R^{9a}$, $-OR^9$ $-S(O)_nR^{12}$, $-COR^9$, $-CO_2R^9$, $-C(O)NR^9R^{9a}$, $-NR^9C(O)R^{9a}$, or $-C(NOR^9)R^{9a}$.

$R^{12}$ is $C_1-C_4$ alkyl;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazclyl, 2,3-dihydrobenzofuranyl or 2,3-dihydrobenzothienyl;

n is independently at each occurrence 0, 1 or 2; and
m is independently at each occurrence 0–6;
with the provisos that:
(1) when $R^4$ is $C_1-C_4$ alkyl and Y is N, then Z is N;
(2) when $R^3$ is phenyl, Y is N, and Z is CH, at least one $R^8$ is other than dimethylamino or $-NCH_3C(O)CH_3$;
(3) when Z and K are CH, $R^5$ is $-OR^7$, and $R^7$ is $CH_2R^{11}$, then $R^{11}$ is not $CO_2R9$; and
(4) when Y and Z are both N, K is CH, and $R^3$ is phenyl, then R1 is not chloro or fluoro.

[3] In a more preferred embodiment, the present invention provides a novel compound of formula I, wherein:
K is $CR^5$;
Y is N;
Z is CH or N;
$R^1$ is methyl;
$R^3$ is an phenyl moiety substituted with 1–3 substituents independently selected from the group consisting of: halo, methoxy, nitro, trifluoromethyl, methyl, amino, methylamino, dimethylamino, cyano, 4-tetrazolyl, carboxy, methylthio, methylsulfonyl, dichloro;
$R^4$ is ethyl;
$R^5$ is selected from the group consisting of $C_{1-4}$ alkyl, $C_{1-4}$ alkoxy, halo, acetyl, dimethylamino, cyano, methylthio, methylsulfonyl.

[4] In an even more preferred embodiment, the present invention provides a novel compound of formula I, wherein:
K is $CR^5$;
Y is $CR^2$;
Z is CH or N;
$R^1$ is methyl;
$R^2$ taken together with $R^4$ is $-A=D-$, where A and D are each CMe or N oriented in such a way as to form an imidazole or a triazole ring, or A is $NR^9$ and D is $C=O$ oriented in such a way as to form an imidazolone;
$R^3$ is an phenyl moiety substituted with 1–3 substituents independently selected from the group consisting of trifluoromethyl, methyl, chloro; and
$R^5$ is selected from the group consisting of $C_{1-4}$ alkyl, $C_{1-4}$ alkoxy, halo, acetyl, dimethylamino, cyano, methylthio, methylsulfonyl.

[5] In another preferred embodiment, the present invention provides a novel compound of formula I, wherein the compound is selected from the group:
N-(2-Bromo-(1-methylethyl)phenyl)-N-ethyl-4-(2-chlorophenyl)-6-methyl-2-pyrimidineamine;
N-(2-Bromo-4,6-dimethoxyphenyl)-N-ethyl-4-(2-(trifluoromethy)phenyl)-6-methyl-2-pyrimidineamine;
N-(2-Bromo-4-(1-methylethyl)phenyl)-N-ethyl-4-(2-(trifluoromethyl)phenyl)-6-methyl-2-pyrimidineamine;
N-(2-Bromo-4-dimethylamino-6-methoxyphenyl)-N-ethyl-4-(2-(trifluoromethyl)phenyl)-6-methyl-2-pyrimidineamine;
N-(2-Bromo-4-(1-methylethyl))-N-ethyl-4-(3-(trifluoromethyl)phenyl)-6-methyl-2-pyrimidineamine;
N-(2-Bromo-4,6-dimethoxyphenyl)-N-ethyl-4-(2-chlorophenyl)-6-methyl-2-pyrimidineamine;
N-[2-Bromo-4-(1-methylethyl)phenyl]-N-ethyl-4-(2-nitrophenyl)-6-methyl-2-pyrimidineamine;
N-(2,4-Dibromophenyl)-N-ethyl-4-[2-(trifluoromethyl)phenyl]-6-methyl-2-pyrimidineamine;
N-(4-Acetyl-2-bromophenyl)-N-ethyl-4-[2-(trifluoromethyl)phenyl]-6-methyl-2-pyrimidineamine;
N-[2-Bromo-4-(1-methylethyl)phenyl]-N-ethyl-4-(2-cyanophenyl)-6-methyl-2-pyrimidineamine;
N-(2-Bromo-4-methylthiophenyl)-N-ethyl-4-[2-(trifluoromethyl)phenyl]-6-methyl-2-pyrimidineamine;
N-(2-Bromo-4-methylsulfonylphenyl)-N-ethyl-4-[2-(trifluoromethyl)phenyl]-6-methyl-2-pyrimidineamine;
N-[2-Bromo-4-(1-methylethyl)phenyl]-N-ethyl-4-(2,4,6-trimethylphenyl)-6-methyl-2-pyrimidineamine;
N-(2,4-Dibromophenyl)-N-ethyl-4-(2-methylthiophenyl)-6-methyl-2-pyrimidineamine;
N-(2-Bromo-4-(1-methylethyl)phenyl)-N-ethyl-4-(2-(trifluoromethyl)phenyl)-6-methyl-1,3,5-triazine-2-amine;
N-(4-dimethylamino-2-(trifluoromethyl)phenyl)-N-ethyl-4-(2-(trifluoromethyl)phenyl)-6-methyl-1,3,5-triazine-2-amine;
9-(2-Bromo-4,-isopropylphenyl)-2-methyl-6-(2-trifluoromethyl)phenyl)-8-azapurine and
N-(2-Bromo-4-(1-methylethyl)phenyl)-N-ethyl-4-(2-methylphenyl)-6-methyl-2-pyrimidineamine; and
N-(2-Bromo-4-)-(1-methylethyl)phenyl)-N-ethyl-4-(2,6-dichlorophenyl)-6-methyl-2-pyrimidineamine.

[6] In a third embodiment, the present invention provides a novel pharmaceutical composition, comprising: a pharmaceutically acceptable carrier and a therapeutically effective amount of a compound of formula (I):

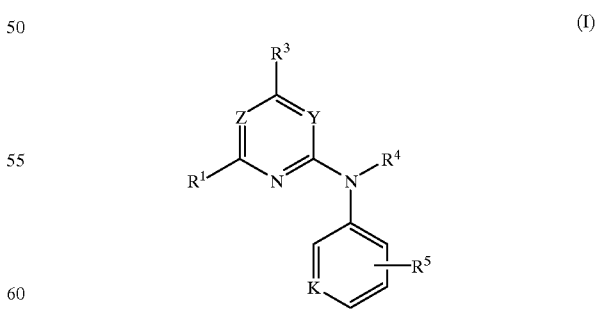

(I)

or a stereoisomer or pharmaceutically acceptable salt form thereof, wherein:
Y is $CR^2$ or N;
Z is CH or N;
K is $CR^5$ or N;

$R^1$ is $C_1$–$C_4$ alkyl, $C_2$–$C_4$ alkenyl, $C_2$–$C_4$ alkynyl, chloro, fluoro, cyano, or trifluoromethyl;

$R^2$ taken together with $R^4$ is —E—F—, where E and F are independently $CR^9$ and $CR^{9a}$; or $R^2$ taken together with $R^4$ is —A═D—, where A and D are each independently CH, $CR^{10}$ or N; provided that —A═D— may not be —CH═N— or $CR^{10}$═N— oriented in such a way as to form a pyrazole ring, but may be —CH═N— or $CR^{10}$═N— oriented in such a way as to form an imidazole ring; or $R^2$ taken together with $R^4$ is —A—D— where A is $NR^9$ and D is C═O oriented in such a way as to form an imidazolone.

$R^3$ is phenyl substituted on 1–4 ring carbons with $R^8$, napthyl substituted on 1–4 ring carbons with $R^8$, pyridinyl substituted on 1–4 ring carbons with $R^8$, or pyrimidinyl substituted on 1–3 ring carbons with $R^8$;

$R^4$ is $C_1$–$C_4$ alkyl, allyl, or propargyl, where $C_1$–$C_4$ alkyl is optionally substituted with $C_3$–$C_6$ cycloalkyl, OH, —$OR^9$, —$S(O)_nR^9$ or —$CO_2R^9$;

$R^5$ represents 1–4 substituents on ring carbons each of which may be independently $C_1$–$C_{10}$ alkyl, $C_2$–$C_{10}$ alkenyl, $C_2$–$C_{10}$ alkynyl, $C_3$–$C_6$ cycloalkyl, $C_4$–$C_{10}$ cycloalkylalkyl, halo, nitro, cyano, —$NR^6R^7$, —$OR^7$, —$COR^7$, —$C(O)NR^6R^7$, —$C(NOR^9)R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{10}$ cycloalkylalkyl are optionally substituted with 1 to 3 substituents independently selected from halo, nitro, cyano, —$NR^6R^7$, —$OR^7$, —$COR^7$, —$C(O)NR^6R^7$, —$S(O)_nR^7$, and —$C(NOR^9)R^7$ and two $R^5$ moieties taken together may comprise $CR^9R^{9a}CR^9R^{9a}O$, $CR^9R^{9a}CR^9R^{9a}CR^9R^{9a}$, or $CR^9$═$CR^{9a}O$;

$R^6$ and R7 are independently at each occurrence H, $C_1$–$C_6$ alkyl, $C_3$–$C_6$ cycloalkyl, —$(CH_2)_m$-phenyl, or —$(CH_2)_m$-heteroaryl; all optionally substituted with 1–3 $R^{11}$'s.

$R^8$ is independently at each occurrence $C_1$–$C_6$ alkyl, $C_2$–$C_6$ alkenyl, $C_2$–$C_6$ alkynyl, $C_3$–$C_6$ cycloalkyl, $C_4$–$C_{10}$ cycloalkylalkyl, phenyl, heteroaryl, halo, nitro, cyano, —$NR^6R^7$, —$OR^7$, —$COR^7$, —$CO_2R^7$, —$C(O)NR^6R^7$, —$OC(O)NR^6R^7$, —$NR^9C(O)NR^6R^7$, —$NR^6C(O)R^7$, —$C(NOR^9)R^7$, —$S(O)_nR^7$, —$NR^9SO_2R^7$, —$SO_2NR^6R^7$, and where $C_1$–$C_6$ alkyl, $C_2$–$C_6$ alkenyl, $C_2$–$C_6$ alkynyl, $C_3$–$C_6$ cycloalkyl, $C_4$–$C_{10}$ cycloalkylalkyl, and phenyl are optionally substituted with 1 to 3 substituents independently selected from halo, nitro, cyano, —$NR^6R^7$, —$OR^7$, —$COR^7$, —$C(O)NR^6R^7$, —$S(O)_nR^7$, —$C(NOR^9)R^7$, —$NR^9SO_2R^7$, and —$SO_2NR^6R^7$; provided that when $R^3$ is pyridinyl, at least one $R^8$ is other than methyl; further provided that when $R^3$ is phenyl, at least one $R^8$ is other than unsubstituted phenyl;

$R^9$ and $R^{9a}$ is H or $C_1$–$C_4$ alkyl;

$R^{10}$ is $C_1$–$C_4$ alkyl, halo, nitro, cyano, —$NR^9R^{9a}$, —$OR^{12}$, or —$S(O)_nR^{12}$;

$R^{11}$ is independently at each occurrence $C_1$–$C_3$ alkyl, halo, nitro, cyano, —$NR^9R^{9a}$, —$OR^9$ —$S(O)_nR^{12}$, —$COR^9$, —$CO_2R^9$, —$C(O)NR^9R^{9a}$, —$NR^9C(O)R^{9a}$, or —$C(NOR^9)R^{9a}$.

$R^{12}$ is $C_1$–$C_4$ alkyl;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl, 2,3-dihydrobenzofuranyl or 2,3-dihydrobenzothienyl;

n is independently at each occurrence 0, 1 or 2; and m is independently at each occurrence 0–6.

Many compounds of this invention have one or more asymmetric centers or planes. Unless otherwise indicated, all chiral (enantiomeric and diastereomeric) and racemic forms are included in the present invention. Many geometric isomers of olefins, C═N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. "Alkenyl" includes hydrocarbon chains of either a straight or branched configuration and one or more unsaturated carbon—carbon bonds which may occur in any stable point along the chain, such as ethenyl, propenyl, and the like. "Alkynyl" includes hydrocarbon chains of either a straight or branched configuration and one or more triple carbon—carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., ═O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4)

cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

The term "pharmaceutically acceptable salts" includes acid or base salts of the compounds of formulas (I) and (II). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal levels of CRF or treat the symptoms of affective disorder, anxiety, depression, immunological, cardiovascular or heart-related diseases and colonic hypersensitivity associated with psychopathological disturbance and stress in a host. in a host.

Synthesis

The compounds of the present invention can be prepared by one of the general schemes outlined below.

Compounds of the Formula (I), wherein Z is CH, and Y is N, and $R^1$ is $C_1$–$C_4$ alkyl can be prepared as shown in Scheme 1.

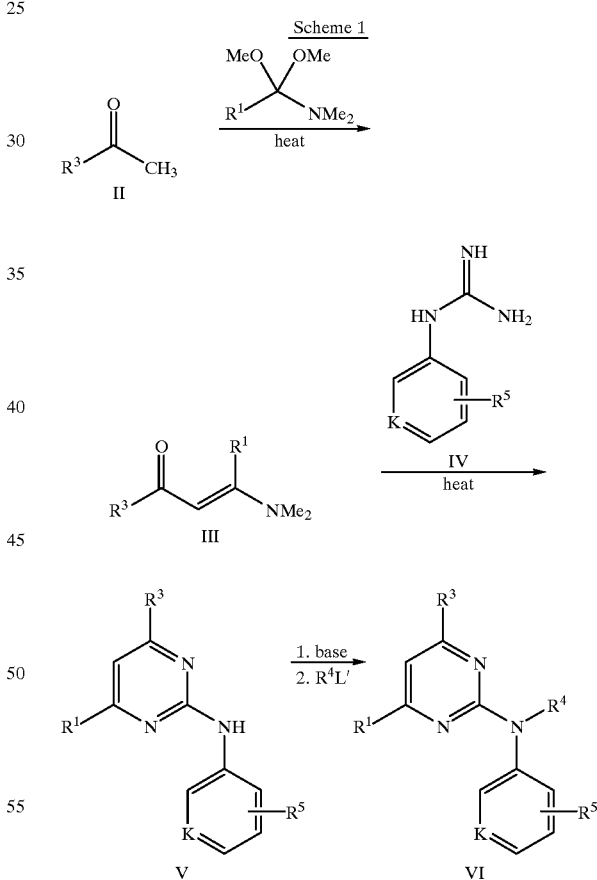

A methyl ketone (II) was converted to the enaminoketone (III) by treatment with a dimethylamide dimethyl acetal as described in U.S. Pat. No. 4,788,195 (Torley et al). Most preferably, (II) was treated with dimethylamide dimethyl acetal in the absence of solvent at temperatures from 80° to reflux. The enaminoketone (III) was reacted with an aryl or heteroaryl guanidine (IV), (in the presence of a base such as potassium carbonate if the guanidine is used as a salt) in N,N-dimethylformamide (DMF) or an alcoholic solvent to afford the corresponding pyrimidine (V). This was treated with a base such as sodium hydride (NaH) or lithium diisopropylamide (LDA) in an aprotic solvent such as tetrahydrofuran (THF), dimethylformamide (DMF), or dimethyl sulfoxide (DMSO) followed by an alkylating agent $R^4L'$, such as an alkyl iodide, mesylate or tosylate to afford (VI) the corresponding alkylated product of Formula (I).

Compounds of Formula (I), wherein Y and Z are both N and $R^1$ is $C_1$–$C_4$ alkyl can be prepared as shown in Scheme 2.

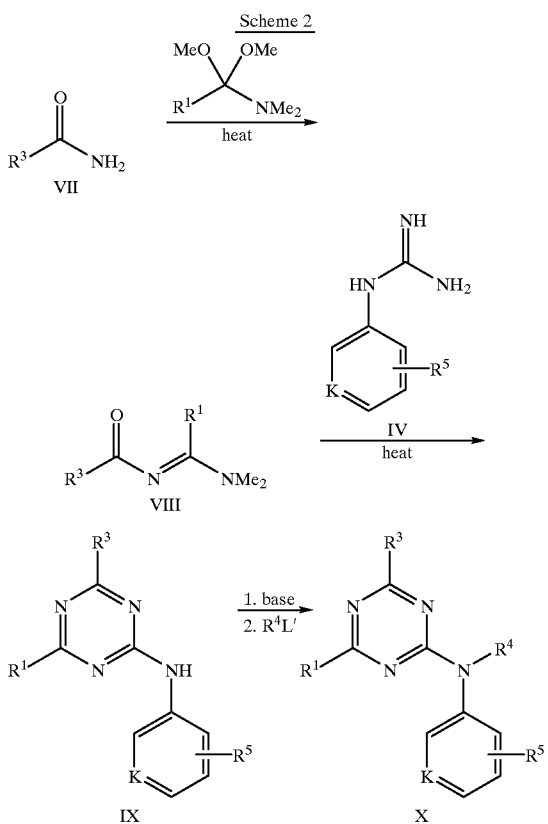

A primary amide (VII) can be converted to an acylamidine (VIII) by treatment with dimethylamide dimethyl acetal. Most preferably, (VII) is treated with dimethylamide dimethyl acetal in the absence of solvent at temperatures from 50° to reflux. The acylamidine (VIII) is reacted with an aryl or heteroaryl guanidine in N,N-dimethylformamide (DMF) or an alcoholic solvent to afford the corresponding triazine (IX). This is subsequently alkylated to afford (X), a compound of Formula (1).

The compounds of Formula (1) where $R^3$ is aryl or heteroaryl, and where Z and Y are each independently CH, $CR^2$, or N; and $R^2$ is $C_1$ to $C_4$ alkyl, chloro, or cyano; or $R^2$ at the Y position taken together with $R^4$ is —A=D—, where A and D are each independently CH, $CR^1$, or N, where $R^1$ is not halo, can be prepared as shown in Scheme 3.

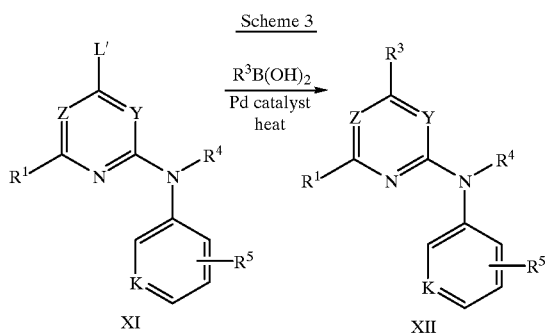

The compound (XI), in which L' is a leaving group such as chloro, bromo, tosyl, mesyl, or triflyl, was treated in an organic solvent such as benzene, toluene, xylene, or dimethoxyethane with an aryl or heteroaryl boronic acid in the presence of a palladium catalyst such as but not limited to tetrakis(triphenylphosphine)palladium, bis(triphenylphosphine)palladium dichloride, or palladium acetate and a base such as aqueous sodium bicarbonate, sodium carbonate, sodium hydroxide, barium hydroxide, or cesium fluoride to afford the arylated or heteroarylated product (XII), a compound of Formula (1). Most preferably, (XI) is treated with boronic acid in refluxing mixture of benzene and ethanol, an aqueous base such as sodium carbonate, and tetrakis(triphenylphosphine)palladium (0).

The heterocyclic chlorides (XI) required for this procedure are described in the patent literature. The preparation of the pyrimidine, 1,3,5-triazine, 8-azapurine, purine, and azaindole chlorides are described in Patent Application WO 95/10506 (Aldrich et al), while the synthesis of pyrrolo[2,3-d]dipyrimidine chlorides are described in patent application WO 94/13676 (Y. L. Chen) and pyrazolo[3,4-d] pyrimidine chlorides are described in patent application WO 94/13677 (Y. L. Chen). Aryl boronic acids are available commercially or may be synthesized by a variety of methods which have been reviewed by N. Miyaura and A. Suzuki, Chemistry Reviews, 95, 2457 (1995).

Pyrimidine compounds of Formula (1) may also be prepared as shown in Scheme 4.

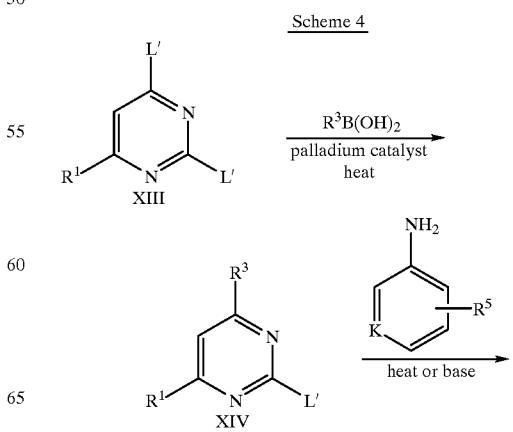

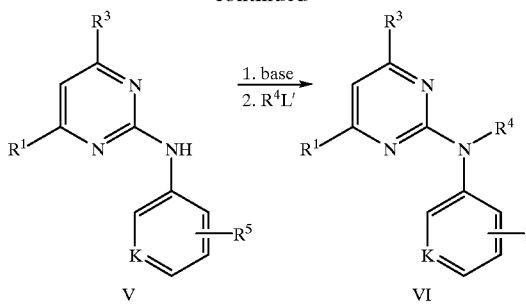

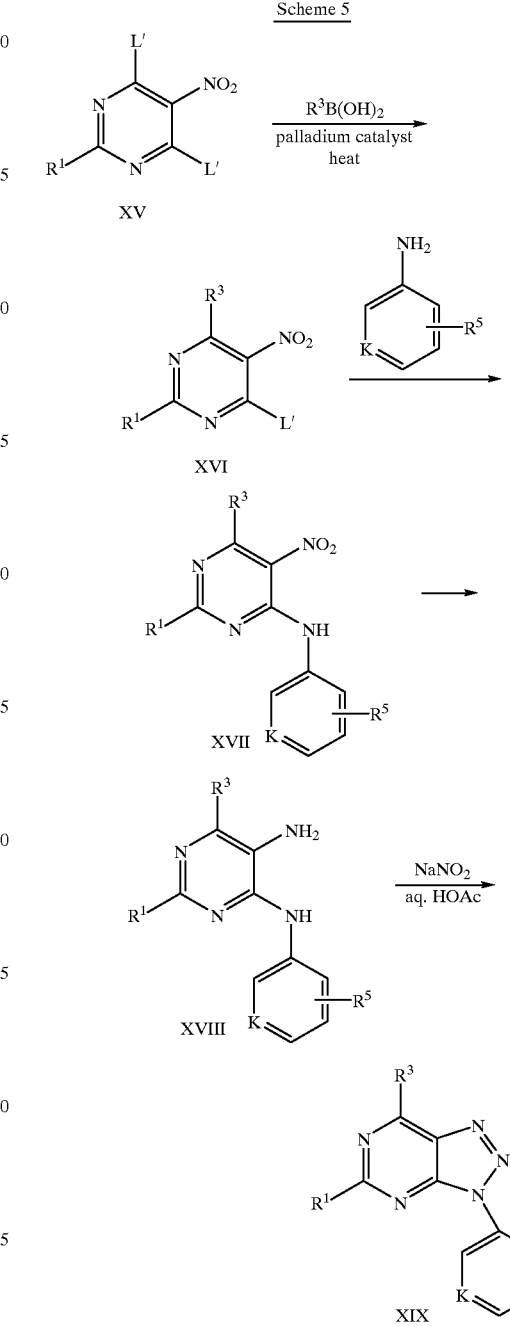

A pyrimidine (XIII) with two leaving groups such as 2,4-dichloro-6-methylpyrimidine was treated with an aryl or heteroaryl boronic acid in the presence of a palladium catalyst to afford the arylated or heteroarylated pyrimidine (XIV). This was reacted with the appropriate aniline or heteroaryl amine in a high-boiling solvent, such as, but not limited to, ethylene glycol, methoxyethoxyethanol etc., or in an aprotic solvent such as THF, dioxane, toluene, xylene, or DMF facilitated by the optional use of a base such as sodium hydride or LDA, which are preferred. The coupled product (V) was subsequently alkylated as described above to afford (VI), a compound of Formula (1). The anilines required for this procedure are either commercially available, or may be synthesized by methods described in Patent Application WO 95/10506 (Aldrich et al).

Compounds of Formula (1) which are pyrimidines may also be prepared as shown in Scheme 4a.

$R^1$ and/or $R^3$ can be attached in either order to the 4- and/or 6-positions by adding an aryl- or alkyllithium reagent and the oxidizing the intermediate dihydropyrimidine. When not commercially available, the required aryl- and alkyllithium reagents can be prepared by conventional methods such as deprotonation, halogen-metal exchange, transmetallation, or by treating a halide with lithium metal. As described by Strekowski et al (J. Heterocylic Chem. 27, 1393 (1990)), despite the presence of a leaving group in the 2-position, attack occurs at an unsubstituted 4- or 6-position in preference to the 2-position. As described above, the resulting pyrimidines (XIV) can be coupled with an aniline or heterocyclic amine and N-alkylated to produce compounds (VI) of Formula (1).

Compounds of Formula (1) which are 8-azapurines may be prepared as shown in Scheme 5.

A 5-nitropyrimidine (XV) with two leaving groups such as a 4,6-dichloro-5-nitropyrimidine [J. Chem. Soc. 3832 (1954); ibid. 677 (1944)] was treated with an aryl or heteroaryl boronic acid in the presence of a palladium catalyst to afford the arylated or heteroarylated pyrimidine (XVI). This was reacted with the appropriate aniline or heteroaryl amine in an appropriate solvent, such as, but not limited to, THF, dioxane, toluene, xylene, or DMF facilitated by the optional use of a base such as triethylamine, diisopropylethylamine, sodium hydride or LDA. The nitro group of the coupled product (XVII) can be reduced by catalytic hydrogenation or with a variety of reducing agents such as stannous chloride, sodium dithionite, or iron in acetic acid, to afford a 5-aminopyrimidine (XVIII). This can be converted with sodium nitrite in aqueous acetic acid to the 8-azapurine (XIX), a compound of Formula (1).

Purines may be prepared as shown in Scheme 6.

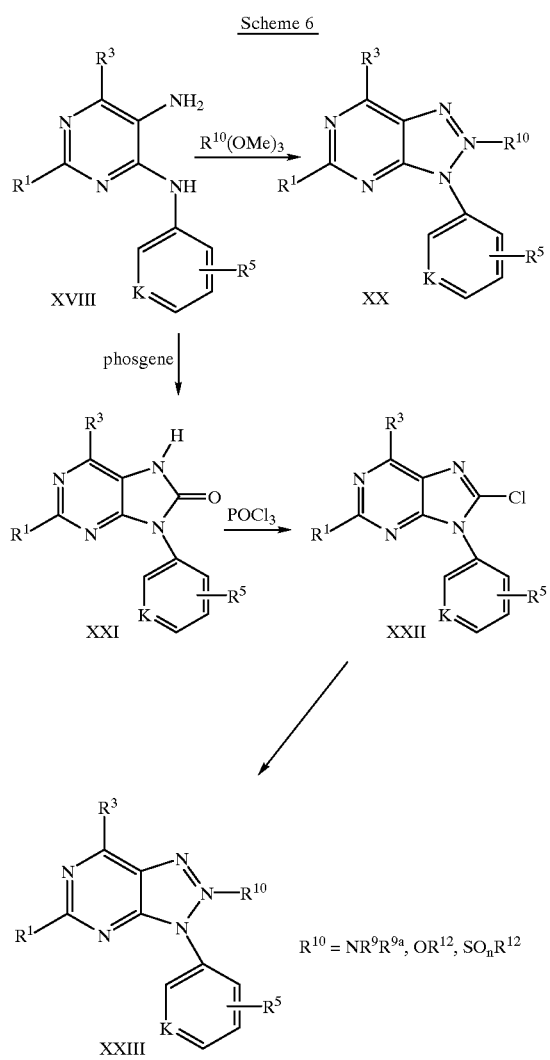

The 5-aminopyrimidine (XIII) can be converted into Purine (XX) where $R^{10}$ is H or alkyl by treatment with an orthoester. Reaction of (XVIII) with a reagent such as phosgene, carbonyldiimidazole, or diethylcarbonate affords a purinone (XXI). Treatment of the purinone with phosphorous oxychloride can give the 8-chloropurine (XXII), a compound of Formula (1) which can in turn be converted by methods well known in the art into a 8-dialkylaminopurine, an 8-alkoxypurine, and an 8-alkylthiopurine (XXIII), by treatment with a dialkylamine, a metal alkoxide such as a sodium alkoxide, or a metal thioalkoxide, respectively. The 8-alkylthiopurines can in turn be converted into the corresponding sulfoxide and sulfone by oxidation methods well known in the art.

The following examples are provided to describe the invention in further detail. These examples, which set forth the best mode presently contemplated for carrying out the invention, are intended to illustrate and not to limit the invention.

EXAMPLE 1

Preparation of N-(2-Bromo-4-(1-methylethyl)phenyl)-N-ethyl-4-(2-bromophenyl)-6-methyl-2-pyrimidineamine Part A: A mixture of 2-bromoacetophenone (7 g) and dimethylacetamide dimethyl acetal (14 mL) was refluxed for 5 hrs, and the cooled reaction mixture was concentrated in vacuo. The crude reaction product was purified by evaporative distillation (0.1 mm/150°) to afford a dark orange liquid (10.2 g) of sufficient purity for further reaction. A portion of this material was purified further by chromatography on silica gel using from 20% ethyl acetate in hexanes to 100% ethyl acetate as eluent to afford the intermediate enaminoketone (2 g) as an amorphous yellow solid. $^1$HNMR (CDCl$_3$), 300 MHz) δ 7.54 (dd, 1H, J=7.7, 1.1 Hz), 7.38 (dd, 1H, J=7.7, 1.1 Hz), 7.29 (dt, 1H, J=7.3, 1.1 Hz), 7.16 (dt, 1H, J=7.4, 1.1 Hz), 5.22 (s, 1H), 3.04 (bs, 6H), 2.67 (s, 3H).

Part B: A mixture of the product from part A (1.09 g), 2-bromo-4-isopropylphenylguanidine hydrochloride (1.17 g), and sodium carbonate (424 mg) in 2-methoxyethanol (30 mL) was refluxed for 19 hr. The cooled reaction mixture was diluted with ethyl acetate and washed with water (2×) and brine, dried and evaporated. The crude reaction product was chromatographed on silica gel using 50% petroleum ether in methylene chloride as eluent. The intermediate anilinopyrimidine was obtained as an oil (337 mg). CI Mass Spec. (M+H)$^+$=462.

Part C: To a solution of the product from part B (320 mg) in dry dimethylsulfoxide (9 mL) was added 100% sodium hydride (40 mg) and iodoethane (0.300 mL). The reaction mixture was stirred for 1.5 hr, and then poured onto brine. This mixture was extracted twice with ethyl acetate, and concentrated in vacuo to 320 mg of a dark oil. The crude product was purified by preparative thin layer chromatography on 4 2 mm thick silica gel plates eluted with 50% petroleum ether in methylene chloride. The title compound was obtained as a pale yellow oil (260 mg). CI-HRMS calcd. for $C_{22}H_{24}N_3Br_2$ (M+H): 488.033695. Found: 488.032196.

EXAMPLE 2

Preparation of N-(2-Bromo-(1-methylethyl)phenyl)-N-ethyl-4-(2-chlorophenyl)-6-methyl-2-pyrimidineamine The title compound was prepared in a manner similar to the product of Example 1. Elemental Analysis: Calcd. for $C_{22}H_{23}N_3ClBr$: C, 59.41: H, 5.21; N, 9.456. Found: C, 59.51; H, 5.21; N, 8.97.

EXAMPLE 3

Preparation of N-(2-Bromo-4-dimethylamino-6-methoxyphenyl)-N-ethyl-4-(2-chlorophenyl)-6-methyl-2-pyrimidineamine The title compound was prepared in a manner similar to the product of Example 1, mp 131–132° Elemental Analysis: Calcd. for $C_{22}H_{24}N_4OCl$ Br: C, 55.53: H, 5.08; N, 11.77. Found: C, 55.40; H, 5.17; N, 11.60.

EXAMPLE 4

N-(2-Bromo-4,6-dimethoxyphenyl)-N-ethyl-4-(2-(trifluoromethyl)phenyl)-6-methyl-2-pyrimidineamine Part A: A mixture of 2,4-dichloro-6-methylpyrimidine (3.26 g, Aldrich), 2-(trifluoromethyl)phenylboronic acid (4.00 g), tetrakis(triphenylphosphine)palladium(0) (500 mg), 1M aqueous sodium carbonate (22 mL), and benzene (60 mL) was refluxed for 7 hr. The cooled mixture was diluted with ethyl acetate and the aqueous layer was removed. The organic layer was washed with water (2×) and brine, dried and concentrated in vacuo. The crude reaction product was chromatographed on silica gel using ethyl acetate/hexanes (1:5) as eluent. The intermediate arylpyrimidine was obtained as a white solid (3.35 g). $^1$HNMR (CDCl$_3$), 300 MHz) δ 7.80 (d, 1H, J=7.0 Hz), 7.64 (m, 2H), 7.51 (d, 1H, J=7.3 Hz), 7.27 (s, 1H), 2.61 (s, 3H).

Part B: A mixture of the product from Part A (300 mg), 2-bromo-4,6-dimethoxyaniline (275 mg) and 100% sodium hydride (75 mg) in dry toluene (8 mL). was refluxed for 5 hr. The excess sodium hydride in the cooled reaction mixture was quenched with a small amount of sodium hydride, and the mixture was partitioned between water and ethyl acetate. The organic layer was washed with brine, dried and evaporated in vacuo, and the crude reaction product was chromatographed on silica gel using ethyl acetate/hexanes (1:4) as eluent. The intermediate anilinopyrimidine was obtained as a pale yellow oil (255 mg). CI Mass Spec. (M+H)$^+$=468, 470.

Part C: To a solution of the product from Part B (250 mg) in dry dimethylsulfoxide (6 mL) was added 100% sodium hydride (40 mg) and iodoethane (0.250 mL). The reaction mixture was stirred for 30 min, quenched with a small amount of methanol, and then poured onto water. This mixture was extracted twice with ethyl acetate, and the combined extracts were washed with brine, dried, and concentrated in vacuo to 210 mg of a dark oil. The crude product was purified by preparative thin layer chromatography on 4 2 mm thick silica gel plates eluted with 25% ethyl acetate in hexanes. The title compound was obtained as an oil (150 mg) which crystallized from ether—petroleum ether to afford colorless crystals (110 mg). mp 137–138°. CI-HRMS calcd. for $C_{22}H_{22}N_3O_3F_3Br$ (M+H): 496.08748. Found: 496.083703.

EXAMPLE 5

Preparation of N-(2-Bromo-4-(1-methylethyl) phenyl)-N-ethyl-4-(2-(trifluoromethyl)phenyl)-6-methyl-2-pyrimidineamine The title compound was prepared in a manner similar to the product of Example 4, mp 101.2–102.5°. Elemental Analysis: Calcd. for $C_{23}H_{23}N_3F_3Br$: C, 57.75: H, 4.856; N, 8.78. Found: C, 58.03; H, 4.90; N, 8.73.

EXAMPLE 6

Preparation of N-(2-Bromo-4-dimethylamino-6-methoxyphenyl)-N-ethyl-4-(2-(trifluoromethyl) phenyl)-6-methyl-2-pyrimidineamine The title compound was prepared in a manner similar to the product of Example 4, mp 157–158.5°. Elemental Analysis: Calcd. for $C_{23}H_{24}OF_3Br$: C, 54.23: H, 4.759; N, 11.00. Found: C, 53.78; H, 4.74; N, 10.75.

EXAMPLE 7

Preparation of N-(2-Bromo-4-(1-methylethyl))-N-ethyl-4-(3-(trifluoromethyl)phenyl)-6-methyl-2-pyrimidineamine The title compound was prepared in a manner similar to the product of Example 4. Elemental Analysis: Calcd. for $C_{23}H_{23}N_3F_3Br$: C, 57.75: H, 4.856; N, 8.78. Found: C, 58.01; H. 4.71; N, 8.76.

EXAMPLE 8

Preparation of N-(2-Bromo-4-(1-methylethyl) phenyl)-N-ethyl-4-(4-(trifluoromethyl)phenyl)-6-methyl-2-pyrimidineamine The title compound was prepared in a manner similar to the product of Example 4. Elemental Analysis: Calcd. for $C_{23}H_{23}N_3F_3Br$: C, 57.75: H, 4.856; N, 8.78. Found: C, 57.66; H, 4.78; N, 8.68.

EXAMPLE 9

Preparation of N-(2-Bromo-4-(1-methylethyl) phenyl)-N-ethyl-4-(2-fluorophenyl)-6-methyl-2-pyrimidineamine The title compound was prepared in a manner similar to the product of Example 4. Elemental Analysis: Calcd. for $C_{22}H_{23}N_3FBr$: C, 61.69: H, 5.41; N, 9.819. Found: C, 61.56; H, 5.12; N, 9.73.

EXAMPLE 10

Preparation of N-(2-Bromo-4,6-dimethoxyphenyl)-N-ethyl-4-(2-chlorophenyl)-6-methyl-2-pyrimidineamine Part A: To a solution of 2-bromo-4,6-dimethoxyaniline (1.16 g) in 10 mL ether was added 6 mL 1N HCl/ether. A precipitate formed and the mixture was concentrated to dryness. To the solid was added ethanol (20 mL), water (20 mL), and cyanamide (673 mg) and the reaction was heated at reflux for 90 minutes. Added 4M HCl/dioxane (2 mL) and cyanamide (673 mg) and heated at reflux for 2 h. Solvent was removed in vacuo and the residue was taken up in 1M pH7 buffer (100 mL) and ether (100 mL). The layers were separated and the aqueous layer was washed further with 2 portions (100 mL each) of ether. The pH of the aqueous layer was adjusted to 13 with solid sodium hydroxide and extracted with 3 portions (100 mL each) of methylene chloride which were combined and concentrated to dryness to afford (2-bromo-4,6-dimethoxyphenyl)guanidine (1.33 g). $^1$H-NMR (CDCl$_3$, 300 MHz), δ 6.80 (d, 1H, J=2.9 Hz), 6.53 (d, 1H, J=2.6 Hz), 4.62 (broad s, 4H), 3.85 (s, 6H).

Part B: The title compound was prepared using the product of part A in a manner similar to the product of Example 1. Elemental analysis: Calcd. for $C_{21}H_{21}N_3O_2ClBr$: C, 54.50; H, 4.57; N, 9.08; Cl, 7.66. Found: C, 54.21; H, 4.65; N, 8.82; Cl, 7.95.

EXAMPLE 11

Preparation of N-[2-Bromo-4-(1-methylethyl) phenyl]-N-ethyl-4-(2-nitrophenyl)-6-methyl-2-pyrimidineamine The title compound was prepared in a manner similar to the product of Example 1. Elemental analysis: Calcd. for $C_{22}H_{23}N_4O_2Br$: C, 58.03; H, 5.09; N, 12.30; Br, 17.55. Found: C, 57.99; H, 5.06; N, 12.17; Br, 17.45.

EXAMPLE 12

N-[2-Bromo-4-(1-methylethyl)phenyl]-N-ethyl-4-(2-aminophenyl)-6-methyl-2-pyrimidineamine The product of Example 11 (778 mg), methanol (40.5 mL), acetic acid (13.5 mL) and iron powder (382 mg) were heated at reflux and stirred mechanically for 6 h. More iron powder (1.15 g) was added and the reaction was heated at reflux 2 more hours, after which it was cooled, filtered through celite, and concentrated to a thick black oil. Added ethyl acetate (200 mL) and water (100 mL), stirred, and filtered through celite. The layers were separated and the ethyl acetate dried over $MgSO_4$ and concentrated to a thick yellow oil (754 mg). The oil was chromatographed on silica gel using ethyl acetate/hexane (1:9) as eluent. The title compound was obtained as an off-white solid (526 mg). CI-HRMS calc'd. for $C_{22}H_{26}N_4Br$ $(M+H)^+$: 425.134083. Found: 425.131850.

EXAMPLE 13

Preparation of N-[2-Bromo-4-(1-methylethyl) phenyl]-N-ethyl-4-(2-methylaminophenyl)-6-methyl-2-pyrimidineamine and Preparation of N-[2-Bromo-4-(1-methylethyl) phenyl]-N-ethyl-4-(2-dimethylaminophenyl)-6-methyl-2-pyrimidineamine The product from Example 12 (288 mg), acetonitrile (20 mL), dimethyl sulfate (128 mg), and sodium bicarbonate (114 mg) were heated at reflux 4 hours. The reaction was concentrated and dissolved in methylene chloride (20 mL) and water (20 mL). The layers were separated and the aqueous layer was again extracted with methylene chloride (20 mL). The combined organic layers were dried and concentrated to a yellow foam (297 mg) which was chromatographed on silica gel using ethyl acetate/hexane (1:9) to afford N-[2-Bromo-4-(1-methylethyl)phenyl]-N-ethyl-4-(2-methylaminophenyl)-6-methyl-2-pyrimidineamine (61 mg) and N-[2-Bromo-4-(1-methylethyl)phenyl]-N-ethyl-4-(2-dimethylaminophenyl)-6-methyl-2-pyrimidineamine (55 mg). CI-HRMS calcd. for $C_{23}H_{28}N_4Br$ $(M+H)^+$: 439.149733. Found: 439.148138 (N-[2-Bromo-4-(1-methylethyl)phenyl]-N-ethyl-4-(2-methylaminophenyl)-6-methyl-2-pyrimidineamine). CI-HRMS calcd. for $C_{24}H_{30}N_4Br$ $(M+H)^+$: 453.165383. Found: 453.163184 (N-[2-Bromo-4-(1-methylethyl)phenyl]-N-ethyl-4-(2-dimethylaminophenyl)-6-methyl-2-pyrimidineamine).

EXAMPLE 15

Preparation of N-(2,4-Dibromophenyl)-N-ethyl-4-[2-(trifluoromethyl)phenyl]-6-methyl-2-pyrimidineamine The title compound was prepared in a manner similar to the product of Example 1. CI-HRMS calc'd for $C_{20}H_{17}N_3F_3Br_2$ $(M+H)^+$: 513.974130. Found: 513.972790.

EXAMPLE 16

Preparation of N-(4-Acetyl-2-bromophenyl)-N-ethyl-4-[2-(trifluoromethyl)phenyl]-6-methyl-2-pyrimidineamine The product of Example 15 (515 mg), bis(triphenylphosphine)Pd(II)dichloride (19 mg), and tetrakis(triphenylphosphine)Pd(0) (27 mg) were combined in a round bottom flask and pumped and purged with nitrogen (3×). Added distilled toluene (2.5 mL), and pumped and purged with nitrogen (2×). Added 1-ethoxyvinyltri-n-butyl tin (0.41 mL), pumped and purged with nitrogen (1×), and heated at reflux 18 hours. Removed solvent in vacuo. Ether (15 mL) and 10% potassium fluoride (aq.) were added and stirred 15 minutes, filtered and the layers separated. The ether layer was dried over $MgSO_4$ and concentrated to dryness, giving the title compound (257 mg). CI-HRMS calcd. for $C_{22}H_{20}N_3OF_3Br$ $(M+H)^+$: 478.074183. Found: 478.072218.

EXAMPLE 17

Preparation of N-[2-Bromo-4-(1-methylethyl) phenyl]-N-ethyl-4-(3-collidyl)-6-methyl-2-pyrimidineamine The title compound was prepared in a manner similar to the product of Example 1. CI-HRMS calcd. for $C_{24}H_{30}N_4Br$ $(M+H)^+$: 453.165383. Found: 453.164255.

EXAMPLE 18

Preparation of N-[2-Bromo-4-(1-methylethyl) phenyl]-N-ethyl-4-(2-cyanophenyl)-6-methyl-2-pyrimidineamine The title compound was prepared in a manner similar to the product of Example 1. CI-HRMS calcd. for $C_{23}H_{24}N_4Br$ $(M+H)^+$: 435.118433. Found: 435.119074.

EXAMPLE 19

Preparation of N-[2-Bromo-4-(1-methylethyl) phenyl]-N-ethyl-4-(2-tetrazolophenyl)-6-methyl-2-pyrimidineamine The product from Example 18 (131 mg), trimethyl tin chloride (150 mg), sodium azide (50 mg), and toluene (2 mL) were heated at reflux for 18 hours. The reaction was concentrated to dryness, taken up in methylene chloride (10 mL) and water (10 mL) and filtered. The organic layer was concentrated to dryness. The crude reaction product was chromatographed on silica gel using ethyl acetate/hexane (2:5) to ethyl acetate to methanbl/methylene chloride (1:19), which afforded the title compound (50 mg). CI-HRMS calcd. for $C_{23}H_{25}N_7{}^{81}Br$ $(M+H)^+$: 480.133434. Found: 480.131722.

EXAMPLE 20

Preparation of N-[2-Bromo-4-(1-methylethyl) phenyl]-N-ethyl-4-(2-carboxyphenyl)-6-methyl-2-pyrimidineamine The product from Example 18 (75 mg) and con. HCl (aq.) (5 mL) were heated at reflux for 18 hours and concentrated to dryness. The crude product was chromatographed on silica gel using ethyl acetate (20%–80%)/hexane and methanol as eluent. The product was recrystallized to give the title compound (12.1 mg), mp 209–210° C. CI-MS $(M+H)^+$, 456.2, 100%.

EXAMPLE 21

Preparation of N-(2-Bromo-4-methylthiophenyl)-N-ethyl-4-[2-(trifluoromethyl)phenyl]-6-methyl-2-pyrimidineamine The product from Example 15 (450 mg), dimethylsulfoxide (12 mL), tetrakis(triphenylphosphine)Pd(0) (40 mg), and sodium thiomethoxide (61 mg) were heated at reflux 18 hours. The reaction was cooled, taken up and partitioned between ethyl acetate (100 mL) and water (100 mL). The ethyl acetate was washed with brine, dried over $MgSO_4$, and concentrated to dryness. The crude product was chromatographed on silica gel giving the title compound (90 mg). CI-HRMS calcd. for $C_{21}H_{20}N_3F_3SBr$ $(M+H)^+$: 482.051340. Found: 482.051434.

EXAMPLE 22

Preparation of N-(2-Bromo-4-methylsulfonylphenyl)-N-ethyl-4-[2-(trifluoromethyl)phenyl]-6-methyl-2-pyrimidineamine The product from Example 21 (75 mg), 85% m-chloroperoxybenzoic acid (63 mg), and methylene chloride (1 mL) were stirred at room temperature for 18 hours and then quenched with 1M sodium sulfite (aq.) (1mL). The mixture was partitioned between methylene chloride (10 mL) and sat. sodium bicarbonate (aq.) (10 mL) and the organic layer was concentrated to dryness. The crude product was chromatographed on silica gel using ethyl acetate/hexane (1:1) as eluent to afford the title compound (60 mg). CI-HRMS calcd. for $C_{21}H_{20}N_3O_2F_3SBr$ $(M+H)^+$: 514.041170. Found: 514.043197.

EXAMPLE 23

Preparation of N-(2-Bromo-4,6-dimethoxyphenyl)-N-ethyl-4-(2-methoxyphenyl)-6-methyl-2-pyrimidineamine Part A: Anisole (2.16 g), n-butyllithium (2.5 M in hexanes, 4.0 mL), and dry ether (4.0 mL) were stirred 18 h at room temperature. Ether (5 mL) and tetrahydrofuran (SmL) were added to make a 0.47 M solution of 2-methoxyphenyllithium (21.12 mL), of which 0.47 mL was added to 2-chloro-4-methylpyrimidine (0.71 g, prepared as described by Strekowski et al (J. Heterocylic Chem. 27, 1393 (1990)) dissolved in dry ether (37 mL) and stirred 30 minutes at −30° C. and 2 hours at 0° C. The reaction was quenched with acetic acid (515 μL), water (36 μL) and tetrahydrofuran (5 mL). 2,3-Dichloro-5,6-dicyano-1,4-benzoquinone (1.31 g) dissolved in tetrahydrofuran (5 mL) was added to the reaction which was then stirred 20 minutes. 1N Sodium hydroxide (aq.) (10 mL) was added at 0° C. and the reaction was washed with iN sodium hydroxide (3×10 mL). The organic layer was filtered through silica gel and concentrated to dryness to give 2-chloro-6-methyl-4-(2-methoxyphenyl)pyrimidine (0.72 g).

Part B: . To 2-bromo-4,6-dimethoxyaniline (348 mg) dissolved in toluene (5 mL) was added sodium hydride (180 mg, 60% in oil). The reaction was stirred for 5 minutes at room temperature and the product of part A (352 mg) was added and heated at reflux 4 hours. The reaction was cooled to room temperature and water (20 mL) was slowly added. The mixture was extracted with ethyl acetate (40 mL) which was dried and concentrated to a brown oil (538 mg). The crude product was chromatographed on silica gel using ethyl acetate/hexane (3:7) as eluent to afford N-(2-Bromo-4,6-dimethoxyphenyl)-4-(2-methoxyphenyl)-6-methyl-2-pyrimidineamine (72 mg).

Part C: The title compound was prepared using the product from part B in a manner similar to the product of part C of Example 1. CI-HRMS calcd. for $C_{22}H_{25}N_3O_3Br$ $(M+H)^+$: 458.107928. Found: 458.107363.

EXAMPLE 24

Preparation of N-[2-Bromo-4-(1-methylethyl)phenyl]-N-ethyl-4-(2,4,6-trimethylphenyl)-6-methyl-2-pyrimidineamine Part A: 2-Bromomesitylene (1.49 g), dry ether (45 mL), and t-butyllithium (1.5 M, 9 mL) were stirred at −78° C. for 10 minutes and 2-chloro-4-methylpyrimidine (643 mg) dissolved in dry ether (10 mL) was added. The reaction was stirred at −30° C. for 1.5 hours and quenched with a mixture of acetic acid (386 μL), water (23 μL), and tetrahydrofuran (5 mL). 2,3-Dichloro-5,6-dicyano- 1,4-benzoquinone (1.25 g) dissolved in tetrahydrofuran (10 mL) was added to the reaction which was then stirred 15 minutes and washed with 1 N sodium hydroxide (three 50 mL portions), dried, and concentrated. The crude product was chromatographed on silica gel using ethyl acetate/hexane (1:9) as eluent affording 2-chloro-6-methyl-4-(2,4,6-trimethylphenyl)pyrimidine (0.99 g) as a white solid.

Part B: The product from part A (740 mg), 2-bromo-4-isopropylaniline (707 mg) and ethylene glycol (4 mL) were heated at reflux for 1 hour and taken up in ethyl acetate (30 mL) and water (30 mL). The layers were separated and the ethyl acetate was washed with 1 N sodium hydroxide (aq.) (two 20 mL portions), dried and concentrated. The crude product was chromatographed on silica gel using ethyl acetate/hexane (1:9) as eluent affording N-[2-Bromo-4-(1-methylethyl)phenyl]-4-(2,4,6-trimethylphenyl)-6-methyl-2-pyrimidineamine (550 mg).

Part C: The title compound was prepared using the product of part B in a manner similar to the product of part C of Example 1. Elemental analysis calcd. for $C_{25}H_{30}N_3Br$: C, 66.37; H, 6.68; N, 9.297. Found: C, 66.39; H, 6.64; N, 9.19.

EXAMPLE 26

Preparation of N-(2,4-Dibromophenyl)-N-ethyl-4-(2-methylthiophenyl)-6-methyl-2-pyrimidineamine The title compound was prepared in a manner similar to the product of Example 25. CI-HRMS calcd. for $C_{20}H_{20}N_3SBr$ $(M+H)^+$: 491.974467. Found: 491.974770.

EXAMPLE 27

Preparation of N-(2,4-Dibromophenyl)-N-ethyl-4-(2-methylsulfonylphenyl)-6-methyl-2-pyrimidineamine The product of Example 26 (740 mg), m-chloroperoxybenzoic acid (85%, 609 mg), and methylene chloride (10 mL) were stirred at room temperature for 18 hours and then quenched with 1M sodium sulfite (aq.) (5 mL). The mixture was partitioned between methylene chloride (40 mL) and sat. sodium bicarbonate (aq.) (40 mL) and the organic layer was concentrated to dryness. The crude product was chromatographed on silica gel using ethyl acetate/hexane (1:1) as eluent to afford the title compound (473 mg). CI-HRMS calcd. for $C_{20}H_{20}N_3O_2SBr$ $(M+H)^+$: 523.964296. Found: 523.966054.

EXAMPLE 28

Preparation of N-(2-Bromo-4-(1-methylethyl)phenyl)-N-ethyl-4-(2,4-dichlorophenyl)-6-methyl-1,3,5-triazine-2-amine Part A: Methyl magnesium bromide (300 mmole, 3M in ether, Aldrich) was added dropwise to a solution of cyanic chloride (12.9 g, 69.9 mmole) in $CH_2Cl_2$ (300 mL) under $N_2$ at −20° C. Addition was complete in ten minutes. Stirring was continued at −20° C. for 4.5 hours. Water (36 mL) was added dropwise while controlling the reaction temperature below −15° C. The reaction mixture was allowed to reach room temperature. Magnesium sulfate (40 g) was added to the reaction mixture and let stand one hour. The reaction mixture was filtered and stripped leaving a yellow solid (11.06 g). This material was purified using flash chromatography ($CH_2Cl_2$, silica) and gave 2,4-dichloro-6-methyl-1,3,5-triazine as a white solid (7.44 g) in 65% yield.

Part B: 2,4-Dichloro-6-methyl-1,3,5-triazine (3 g, 18.29 mmol), 2-bromo-N-ethyl-4-isopropylaniline (6.07 g, 25.07 mmol) and diisopropylethylamine (3.2 g, 25.07 mmol) were dissolved in dioxane (60 mL) under $N_2$ and refluxed three hours. The solvent was stripped and the residue was purified using flash chromatography ($CH_2Cl_2$, silica). to provide N-(2-bromo-4-isopropylphenyl)-N-ethyl-4-chloro-6-methyl-1,3,5-triazine-2-amine (4.58 g) as a clear oil in 68% yield.

Part C: A mixture of N-(2-bromo-4-isopropylphenyl)-N-ethyl-4-chloro-6-methyl-1,3,5-triazine-2-amine (370 mg), 2,4-dichlorophenylboronic acid (210 mg) tetrakis(triphenylphoshine)palladium(0) (50 mg), 1M aqueous sodium carbonate (2 mL), ethanol (0.75 mL) and benzene (6 mL) was refluxed for 10 hr. The cooled mixture was diluted with ethyl acetate and the aqueous layer was removed. The organic layer was washed with water and brine, dried, and concentrated in vacuo The crude reaction product was chromatographed on silica gel using ethyl acetate/hexanes (1:9) as eluent. The title compound was obtained as a pure colorless viscous oil (210 mg) that crystallized on standing and trituration with petroleum ether to colorless crystals (82 mg). Elemental Analysis: Calcd. for $C_{21}H_{21}N_4Cl_2Br$: C, 52.52: H, 4.417; N, 11.67. Found: C, 52.79; H, 4.34; N, 11.40.

EXAMPLE 29

Preparation of N-(2-Bromo-4-(1-methylethyl) phenyl)-N-ethyl-4-(2-(trifluoromethyl)phenyl)-6-methyl-1,3,5-triazine-2-amine The title compound was prepared in a manner similar to the product of Example 28. CI-HRMS calcd. for $C_{22}H_{23}N_4F_3Br_1$ (M+H): 479.105818. Found: 479.104501.

EXAMPLE 30

Preparation of N-(4-dimethylamino-2-(trifluoromethyl)phenyl)-N-ethyl-4-(2-(trifluoromethyl)phenyl)-6-methyl-1,3,5-triazine-2-amine The title compound was prepared in a manner similar to the product of Example 28. Elemental Analysis: Calcd. for $C_{22}H_{21}N_5F_6$: C, 56.29: H, 4.519; N, 14.92. Found: C, 56.14; H, 4.53; N, 14.87.

EXAMPLE 31

Preparation of 4-(2-(Trifluoromethyl)phenyl)-2,5,6-trimethyl-7-(2,4,6-trimethylphenyl)-7H-pyrrolo[2,3-d]pyrimidine A mixture of 4-chloro-2,5,6-trimethyl-7-(2,4,6-trimethylphenyl)-7H-pyrrolo[2,3-d]pyrimidine (425 mg, prepared as described by Y. L. Chen in Patent Application WO94/13676), 2-(trifluoromethyl)phenylboronic acid (310 mg) tetrakis(triphenylphoshine)palladium(0) (50 mg), 1M aqueous sodium carbonate (2 mL), ethanol (0.75 mL) and benzene (6 mL) was refluxed for 6 hr. The cooled mixture was diluted with ethyl acetate and the aqueous layer was removed. The organic layer was washed with 1N aqueous sodium hydroxide, and brine, dried, and concentrated in vacuo. The crude reaction product was chromatographed on silica gel using ethyl acetate/hexanes (1:3) as eluent. The title compound was obtained as a glass (300 mg) that crystallized on trituration with ether to give crystals, mp 176.5–177.5°. Elemental Analysis: Calcd. for $C_{22}H_{24}N_3F_3$: C, 70.91: H, 5.71; N, 9.92. Found: C, 70.69; H, 5.72; N, 9.84.

EXAMPLE 32

Preparation of 6-(2-)-2-methyl-9-(2,4,6-trimethylphenyl)-8-azapurine

Part A: 4,6-Dichloro-2-methyl-5-nitropyrimidine (10 g, 48 mmol) dissolved in DMSO/water (480 ml/48 ml) followed by addition of 2,4,6-trimethylaniline (7.43 ml, 52.8 mmol) dropwise via syringe over 30 minutes. The reaction was stirred at RT for 18 hours and filtered. The solid was washed with water until the filtrate volume reached 600 ml. A 150 ml aliquot was removed, diluted with 1.5 liters water and 100 ml saturated brine, and extracted with 4×100 ml methylene chloride. This procedure was repeated until the remainder of the filtrate had been worked up. The combined organic extracts were dried over anhydrous magnesium sulfate, filtered and concentrated in vacuo. The crude solid was chromatographed on silica gel (350 g, 97/3 methylene chloride/methanol) to give the desired yellow crystalline product, 10.53 g (76%). $^1$H NMR ($CDCl_3$, 300 MHz) δ 12.23 (bs, 1H), 10.60 (s, 1H), 6.95 (s, 2H), 2.34 (2, 3H), 2.33 (s, 3H), 2.16 (s, 6H).

Part B: A solution of the product from Part A (1.50 g) in phosphorous oxychloride (20 mL) was heated at 90° for 35 min. The bulk of the excess phosphorous oxychloride was removed on the rotary evaporator, and the thick oil which remained was stirred vigorously with ice water providing a brown solid (1.29 g) which was used without purification in the next reaction.

Part C: The product from Part B (1.23 g) was dissolved in a mixture of methanol (30 mL) and acetic acid (1.5 mL). To this solution at 0° was added iron powder (0.78 g), the mixture was first allowed to come to room temperature, and then was refluxed for 2.5 hr. Additional iron powder (0.78 g) and acetic acid (1.5 mL) was added and reflux was continued for another 1.5 hr. The cooled reaction mixture was filtered through a pad of filter-aid, and the filter cake was washed with ethyl acetate. The combined filtrates were concentrated in vacuo, and partitioned between ethyl acetate and water, the aqueous layer was extracted three times with ethyl acetate and the combined extracts were dried over sodium sulfate and concentrated in vacuo to a brown solid. Chromatography on silica gel (ethyl acetate/hexanes 1:1) afforded the intermediate diaminopyrimidine (0.56 g).

Part D: To a 2-phase mixture of the product from Part C (0.56 g) in methylene chloride (10 mL) and 50% aqueous acetic acid (8 mL) was added dropwise, a solution of sodium nitrite (152 mg) in water (1 mL). After vigorous stirring for 30 min, the reaction mixture was poured onto water and extracted twice with methylene chloride. The combined extracts were washed with brine, dried and evaporated to 6-chloro-2-methyl-9-(2,4,6-trimethylphenyl)-8-azapurine (0.50 g) as a tan solid, which was used without purification in the next reaction.

Part E: A mixture of 6-chloro-2-methyl-9-(2,4,6-trimethylphenyl)-8-azapurine (450 mg), 2-methylphenylboronic acid (234 mg), tetrakis(triphenylphoshine)palladium(0) (120 mg), 1M aqueous sodium carbonate (2.6 mL), ethanol (1.2 mL) and benzene (8 mL) was refluxed for 2 hr. An additional 50 mg of tetrakis(triphenylphoshine)palladium(0) was added, and the mixture was refluxed overnight. The cooled mixture was diluted with ethyl acetate and the aqueous layer was removed. The organic layer was washed with water and brine, dried, and concentrated in vacuo. The crude reaction product was chromatographed on silica gel using first methylene chloride, then 2% methanol in methylene chloride as eluents. The title compound was obtained as a yellow solid (364 mg) that was recrystallized from ether/petroleum ether (215 mg), mp 140.5–141.7°. Elemental Analysis: Calcd. for $C_{21}H_{21}N_5$: C, 73.44: H, 6.16; N, 20.39. Found: C, 73.23; H, 6.22; N, 20.35.

EXAMPLE 33

Preparation of 6-(2,4-dichlorophenyl)-2-methyl-9-(2,4,6-trimethylphenyl)-8-azapurine The title compound was prepared in a manner similar to the product of Example 32; mp 166.8–168.2°. Elemental Analysis: Calcd. for $C_{20}H_{17}N_5Cl_2$: C, 60.31: H, 4.30; N, 17.58. Found: C, 59.75; H, 4.40; N, 17.33.

EXAMPLE 34

Preparation of 6-(2-methylphenyl)-2-methyl-9-(2-chloro-4,6-dimethoxyphenyl)-8-azapurine The title compound was prepared in a manner similar to the product of Example 32; mp 172.9–173.8°. Elemental Analysis: Calcd. for $C_{20}H_{18}N_5O_2Cl$: C, 60.68: H, 4.58; N, 17.69. Found: C, 60.18; H, 4.54; N, 17.38.

EXAMPLE 35

Preparation of 6-(2-(trifluoromethyl)phenyl)-2-methyl-9-(2,4,6-trimethylphenyl)-8-azapurine The title compound was prepared in a manner similar to the product of Example 32; mp 138.6–139.3°. Elemental Analysis: Calcd. for $C_{21}H_{18}N_5F_3$: C, 63.47: H, 4.51; N, 17.62. Found: C, 63.41; H, 4.51; N, 17.64.

EXAMPLE 36

Preparation of 9-(2-Bromo-4,6-dimethoxyphenyl)-7,9-dihydro-2-methyl-6-(2-(trifluoromethyl)phenyl)-8H-purin-8-one Part A: To a solution of 4,6-dichloro-2-methyl-5-nitropyrimidine (3.12 g, 15 mmol, J. Chem. Soc 3832 (1954); ibid 677 (1944)) and 2-(trifluoromethyl) phenylboronic acid (3.42 g, 18 mmol) in benzene (50 ml) was added 1M aqueous sodium carbonate (20 ml) and 500 mg of tetrakis(triphenylphosphine)palladium. This mixture was refluxed for 4.5 hours, then was diluted with ethyl acetate, washed with water and brine, dried over sodium sulfate, filtered, and concentrated in vacuo. Chromatography on silica gel (10% then 20% ethylacetate in hexanes) afforded 4-Chloro-2-methyl-5-nitro-6-(2-(trifluoromethyl) phenyl)-pyrimidine (1.90 g) as a pale yellow solid. CI Mass Spec. (M+H)$^+$=318.0.

Part B: The product from Part A (2.89 g), 2-bromo-4,6-dimethoxyaniline (2.59 g), and diisopropylethylamine (1.89 ml) in dioxane (90 ml) was refluxed overnight. The cooled solution was poured onto water and extracted 2 times with ethyl acetate. The combined extracts were washed with saturated aqueous sodium chloride, dried over sodium sulfate, filtered, and concentrated in vacua. The dark-colored oil was chromatographed on silica gel (10% to 50% ethyl acetate in hexanes) affording 4.5 g of an orange amorphous solid. Recrystallization from ethyl acetate/ether/petroleum ether afforded 3.08 g of 4-(2-Bromo-4,6-dimethoxyphenyl) amino-2-methyl-5-nitro- 6-(2-(trifluoromethyl)phenyl) pyrimidine as an orange solid, mp 146.8–147.8°. Elemental Analysis: Calcd. for $C_{20}H_{16}N_4O_4F_3Br_1$: C, 46.80: H, 3.14; N, 10.92. Found: C, 46.76; H, 3.15; N, 10.76.

Part C: A mixture of the product from Part B (2.84 g), iron filings (5 g), acetic acid (7 ml), and methanol (100 ml) was brought to reflux. When no reaction was observed to occur by tlc, a small amount of HCl treated iron filings were added to the reaction mixture. After 2.5 hours at reflux, the cooled reaction mixture was filteed through filter-aid. The filter pad was washed with methanol and methylene chloride, and the combined filtrates were concentrated in vacuo. The crude product was partitioned between ethyl acetate and water, the aqueous layer was reextracted with ethyl acetate and the combined extracts were washed with saturated aqueous sodium chloride, dried over sodium sulfate, filtered, and concentrated in vacuo. The orange solid was redissolved in ethyl acetate, and this solution was washed twice with aqueous sodium bicarbonate and concentrated in vacuo to afford 1.84 g of an orange solid, 5-Amino-4-(2-bromo-4,6-dimethoxyphenyl)amino-2-methyl-6-(2-(trifluoromethyl) phenyl)-pyrimidine, which was used without purification in Part D. A portion of this material was recrystallized from ethyl acatete/hexanes to afford a white solid. CI Mass Spec. (M+H)$^+$=483.1.

Part D: A mixture of the product from Part C (250 mg), phosgene (2.7 ml of a 1.93M solution in toluene), and in dry toluene (6 ml) was refluxed for 30 minutes. The cooled mixture was poured onto water and extracted 3 times with ethyl acetate. The combined extracts were dried over sodium sulfate, filtered, and concentrated in vacuo. The crude product was purified by preparative TLC on silica gel (3/1 ethyl acetate/hexanes) to afford the title compound (128 mg) as a solid, mp 255–256°. CI-HRMS calcd. for $C_{21}H_{17}N_4O_3F_3Br_1$ (M+H): 509.044. Found: 509.044742.

EXAMPLE 37

Preparation of 9-(2-Bromo-4,6-dimethoxyphenyl)-7, 9-dihydro-2,7-dimethyl-6-(2-trifluoromethyl) phenyl)-8H-purin-8-one To a solution of the product from Example 36, Part D (107 mg) in acetone (5 ml) was added powdered potassium hydroxide (24 mg) and methyl iodide (0.027 ml). The reaction mixture was stirred at room temperature for 2 hours, then concentrated in vacuo. The crude product was taken up in a mixture of water (15 ml) and saturated sodium chloride (5 ml) which was extracted 3 times with ethyl acetate. The combined extracts were dried over sodium sulfate, filtered and concentrated in vacuo. to an oil which crystallized from ether. Recrystallization from ether afforded the title compound (74 mg) as a white crystalline solid, mp 199–200°. Elemental Analysis: Calcd. for $C_{22}H_{18}N_4O_3F_3Br_1$: C, 50.49: H, 3.477; N, 10.71. Found: C, 50.81; H, 3.58; N, 10.34.

EXAMPLE 38

Preparation of 9-(2-Bromo-4,6-dimethoxyphenyl)-2, 8-dimethyl-6-(2-trifluoromethyl)phenyl)purine To a solution of the product from Example 36, Part C (200 mg) in methylene chloride (4 mL) was added 4M hydrogen chloride in dioxane (0.5 mL) and triethylorthoacetate (4 mL). The reaction mixture was stirred for 1.5 hr at room temperature and then was poured onto saturated sodium bicarbonate. This mixture was extracted twice with methylene chloride, and the combined extracts were dried over sodium sulfate and concentrated in vacuo to a tan solid.

This material was combined with xylenes (20 mL) and refluxed overnight. The cooled mixture was concentrated in vacuo, and the crude reaction product was chromatographed on silica gel using first 50% then 70% ethyl acetate in hexanes. Two recrystallizations from ether afforded the title compound as colorless crystals (70 mg), mp 149–150°. Elemental Analysis: Calcd. for $C_{22}H_{18}N_4F_3BrO_2$: C, 52.09: H, 3.586; N, 11.04. Found: C, 51.78; H, 3.64; N, 10.94.

EXAMPLE 39

Preparation of 9-(2-Bromo-4,6-dimethoxyphenyl)-2-methyl-6-(2-trifluoromethyl)phenyl)-8-azapurine To a solution of the product from Example 36, Part C (250 mg) in methylene chloride (10 mL) and 50% aqueous acetic acid (4 mL) was added dropwise, a solution of sodium nitrite (40 mg) in water (0.5 mL). The mixture was stirred at room temperature for 30 min and poured onto water. This was extracted twice with metylene chloride, and the combied extracts were washed with brine, dried and concentrated in vacuo to an orange solid (235 mg). Recrystallization first from ether, and then from ethyl acetate—hexane afforded a colorless solid (130 mg), mp 157.8–158.3°. Elemental Analysis: Calcd. for $C_{20}H_{15}N_5F_3BrO_2$: C, 48.60: H, 3.069; N, 14.17. Found: C, 48.77; H, 3.15; N, 13.98.

EXAMPLE 40

Preparation of 9-(2-Bromo-4,-isopropylphenyl)-2-methyl-6-(2-trifluoromethyl)phenyl)-8-azapurine The title compound was prepared in a manner similar to the product of Example 39; mp 152.2–153.2°. Elemental Analysis: Calcd. for $C_{21}H_{17}BrF_3$: C, 52.96: H, 3.607; N, 14.70. Found: C, 52.95; H, 3.52; N, 14.65.

EXAMPLE 41

Preparation of 9-(2-Bromo-4-isopropylphenyl)-7,9-dihydro-2,7-dimethyl-6-(2-trifluoromethyl)phenyl)-8H-purin-8-one Part A: The product from Example 36, Part A (1.9 g) and 2-bromo-4-isopropylaniline (1.5 g) in tetrahydrofuran (20 ml) was refluxed for 5 hours. The cooled solution was diluted with ethyl acetate, washed with dilute aqueous sodium bicarbonate and saturated aqueous sodium chloride, dried over sodium sulfate, filtered, and concentrated in vacuo. Trituration with a mixture of ether and petroleum ether afforded the desired product (2.63 g) as orange crystals which were used directly in Part B. A portion of this material was recrystallized from isopropanol giving 4-(2-bromo-4-isopropylphenyl)amino-2-methyl-5-nitro-6-(2-(trifluoromethyl)phenyl)pyrimidine as orange-yellow crystals, mp 145.5–146.5°. Elemental Analysis: Calcd. for $C_{21}H_{18}N_4O_2F_3Br_1$: C, 50.92: H, 3.66; N, 11.31. Found: C, 50.91; H, 3.55; N, 11.10.

Part B: To a solution of the product from Part A (1.0 g) in dioxane (50 ml) was added in succession: water (50 ml), concentrated aqueous ammonia (3 ml), and sodium dithionite (2.78 g). After stirring 30 minutes at room temperature, the reaction mixture was poured onto water and extracted three times with ethyl acetate. The combined extracts were washed with brine, dried, and concentrated in vacua. The crude oil was chromatographed on silica gel (25% then 50% ethyl acetate in hexanes) to afford 5-amino-4-(2-bromo-4-isopropylphenyl)amino-2-methyl-6-(2-(trifluoromethyl) phenyl)-pyrimidine as an off-white solid (350 mg). $^1$HNMR (CDCl$_3$), 300 MHz) δ 8.57 (d, 1H, J=8.8 Hz), 7.82 (d, 1H, J=7.7 Hz), 7.63 (m, 3H), 7.42 (m, 2H), 7.24 (m, 1H), 2.87 (m, 1H), 2.83 (bs, 2H), 2.59 (s, 3H), 1.26 (d, 6H, J=7.0 Hz).

Part C: A mixture of the product from Part B (200 mg), phosgene (2.2 ml of a 1.93M solution in toluene), and in dry toluene (6 ml) was refluxed for 2 hours. The cooled mixture was poured onto water and extracted 3 times with ethyl acetate. The combined extracts were dried over sodium sulfate, filtered, and concentrated in vacuo to 9-(2-bromo-4-isopropylphenyl)-7,9-dihydro-2-methyl-6-(2-trifluoromethyl)phenyl)-8H-purin-8-one (250 mg) as an off-white solid which was used without purification in Part D. $^1$HNMR (CDCl$_3$), 300 MHz) δ 8.17 (bs, 1H), 7.83 (d, 1H, J=7.0 Hz), 7.15–7.7 (m, 6H), 3.00 (m, 1H), 2.67 (s, 3H), 1.32 (d, 6H, J=6.5 Hz).

Part D: To a solution of the product from Part C (174 mg) in acetone (5 ml) was added powdered potassium hydroxide (39 mg) and methyl iodide (0.044 ml). The reaction mixture was stirred at room temperature for 3 hours, then concentrated in vacuo. The crude product was taken up in a mixture of water (20 ml) and saturated sodium chloride (5 ml) which was extracted 3 times with ethyl acetate. The combined extracts were dried over sodium sulfate, filtered and concentrated in vacuo, the white solid product was chromatographed on silica gel (33% then 50% ethyl acetate in hexanes) affording 158 mg of a solid which was recrystallized from ether/petroleum ether to give 103 mg of the title compound as white crystalline solid, mp 163–164°. Elemental Analysis: Calcd. for $C_{23}H_{20}N_4O_1F_3Br_1$: C, 54.67: H, 3.99; N, 11.09. Found: C, 54.71; H, 4.09; N, 10.97.

Preparation A
2-(Trifluoromethyl)phenylboronic acid

To a stirred solution of 2-Bromo-(trifluoromethyl) benzene (18.2 mL, 0.133 moles) in dry THF (150 mL) at −78° was added dropwise over a 25 min period n-butyllithium (60 mL of 2.5M in hexanes, 0.147 moles). The solution was stirred at −78° for 1 hour, and then a solution of triisopropyborate (37 mL) in THF (50 mL) was added dropwise over 30 min at −78°. The cooling bath was removed and the reaction mixture was stirred at ambient temperature overnight. The solution was then cooled to 0°, and made acidic with 1N aqueous hydrochloric acid. The resulting mixture was extracted twice with ether, and the combined extracts were extracted twice with 1N sodium hydroxide. The combined aqueous extracts were acidified to pH 2 with 1N hydrochloric acid and extracted twice with ether. The combined extracts were dried over magnesium chloride, and concentrated in vacuo to a white solid (20.95 g). Two recrystallizations from water afforded the title compound as a colorless solid (11.35 g).

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12-18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 mM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 mg/l aprotinin, 1 mg/ml leupeptin and 1 mg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 mg/ml to be used in the assay.

Binding assays are performed in 96 well plates; each well having a 300 ml capacity. To each well is added 50 ml of test drug dilutions (final concentration of drugs range from $10^{-10}$–$10^{-5}$ M), 100 ml of $^{125}$I-ovine-CRF ($^{125}$I-o-CRF) (final concentration 150 pM) and 150 ml of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, Anal. Biochem. 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity was performed as described by G. Battaglia et al. Synapse 1:572 (1987). Briefly, assays were carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6m}$) and 0.8 mg original wet weight tissue (approximately 40–60 mg protein). Reactions were initiated by the addition of 1 mM ATP/[$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

Some compounds of this invention were tested in this assay and found to be active.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990)

Compounds may be tested in any species of rodent or small mammal. Disclosure of the assays herein is not intended to limit the enablement of the invention.

Compounds of this invention have utility in the treatment of abnormalities in humans and other mammals which are associated with corticotropin releasing factor and/or a receptor for corticotropin releasing factor. This includes depression, affective disorders, anxiety, irritable bowel syndrome, post-traumatic stress disorder, supranuclear palsy, epilepsy, seizures, immune suppression, Alzheimer's disease, gastrointestinal disease, anorexia nervosa or other feeding disorder, drug or alcohol withdrawal symptoms, drug addiction, inflammatory disorders, fertility problems. It includes numerous other disorders such as those mentioned in the disclosure of Pfizer WO95/33750, at pages 7 and 8, which is incorporated herein by reference.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease and immunological or cardiovascular disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A method of treating affective disorder, anxiety or depression in mammals, comprising: administering to the mammal a therapeutically effective amount of a compound of formula (I):

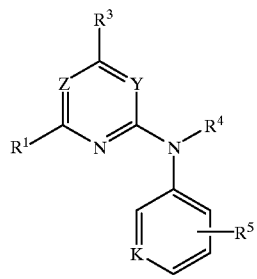

or a stereoisomer or pharmaceutically acceptable salt form thereof, wherein:
Y is $CR^2$ or N;
Z is CH or N;
K is $CR^5$ or N;
$R^1$ is $C_1$–$C_4$ alkyl, $C_2$–$C_4$ alkenyl, $C_2$–$C_4$ alkynyl, chloro, fluoro, cyano, or trifluoromethyl;
$R^2$ taken together with $R^4$ is —E—F—, where E and F are independently $CR^9$ and $CR^{9a}$; or $R^2$ taken together with $R^4$ is —A=D—, where A and D are each independently CH, $CR^{10}$ or N; provided that —A=D— may not be —CH=N— or —$CR^{10}$=N— oriented in such a way as to form a pyrazole ring, but may be —CH=N— or —$CR^{10}$=N— oriented in such a way as to form an imidazole ring; or $R^2$ taken together with $R^4$ is —A—D— where A is $NR^9$ and D is C=O oriented in such a way as to form an imidazolone;
$R^3$ is phenyl which is substituted on 1–4 ring carbons of the phenyl with $R^8$, napthyl which is substituted on 1–4 ring carbons of the napthyl with $R^8$, pyridinyl which is substituted on 1–4 ring carbons of the pyridine with $R^8$ or pyrimidinyl substituted on 1–4 ring carbons of the pyrimidine with $R^8$;
$R^4$ is $C_1$–$C_4$ alkyl, allyl, or propargyl, where $C_1$–$C_4$ alkyl is optionally substituted with $C_3$–$C_6$ cycloalkyl, OH, —$OR^9$, —$S(O)_nR^9$ or —$CO_2R^9$;
$R^5$ represents 1–4 substituents on ring carbons each of which may be independently $C_1$–$C_{10}$ alkyl, $C_2$–$C_{10}$ alkenyl, $C_2$–$C_{10}$ alkynyl, $C_3$–$C_6$ cycloalkyl, $C_4$–$C_{10}$ cycloalkylalkyl, halo, nitro, cyano, —$NR^6R^7$, —$OR^7$, —$COR^7$, —$C(O)NR^6R^7$, —$C(NOR^9)R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{10}$ cycloalkylalkyl are optionally substituted with 1 to 3 substituents independently selected from the group consisting of halo, nitro, cyano, —$NR^6R^7$, —$OR^7$, —$COR^7$, —$C(O)NR^6R^7$, —$S(O)_nR^7$, and —$C(NOR^9)R^7$ and two $R^5$ moieties taken together may comprise —$CR^9R^{9a}CR^9R^{9a}O$—, —$CR^9R^{9a}CR^9R^{9a}CR^9R^{9a}O$—, or —$CR^9$=$CR^{9a}O$—;
$R^6$ and $R^7$ are independently at each occurrence selected from the group consisting of H, $C_1$–$C_6$ alkyl, $C_3$–$C_6$ cycloalkyl, —$(CH_2)_m$-phenyl, and —$(CH_2)_m$-heteroaryl; all optionally substituted with 1–3 $R^{11}$'s;
$R^8$ is independently at each occurrence selected from the group consisting of $C_1$–$C_6$ alkyl, $C_2$–$C_6$ alkenyl, $C_2$–$C_6$ alkynyl, $C_3$–$C_6$ cycloalkyl, $C_4$–$C_{10}$ cycloalkylalkyl, phenyl, heteroaryl, halo, nitro, cyano, —$NR^6R^7$, —$OR^7$, —$COR^7$, —$CO_2R^7$, —$C(O)NR^6R^7$, —$OC(O)NR^6R^7$, —$NR^9C(O)$ $NR^6R^7$, $-NR^6C(O)R^7$, $-C(NOR^9)R^7$, $-S(O)_nR^7$, $-NR^9SO_2R^7$, and $-SO_2NR^6R^7$, and where $C_1-C_6$ alkyl, $C_2-C_6$ alkenyl, $C_2-C_6$ alkynyl, $C_3-C_6$ cycloalkyl, $C_4-C_{10}$ cycloalkylalkyl, and phenyl are optionally substituted with 1 to 3 substituents independently selected from the group consisting of halo, nitro, cyano, $-NR^6R^7$, $-OR^7$, $-COR^7$, $-C(O)NR^6R^7$, $-S(O)_nR^7$, $-C(NOR^9)R^7$, $-NR^9SO_2R^7$, and $-SO_2NR^6R^7$; provided that when $R^3$ is pyridinyl, at least one $R^8$ is other than methyl; further provided that when $R^3$ is phenyl, at least one $R^8$ is other than unsubstituted phenyl;

$R^9$ and $R^{9a}$ is H or $C_1-C_4$ alkyl;

$R^{10}$ is $C_1-C_4$ alkyl, halo, nitro, cyano, $-NR^9R^{9a}$, $-OR^{12}$, or $-S(O)_nR^{12}$;

$R^{11}$ is independently at each occurrence selected from the group consisting of $C_1-C_3$ alkyl, halo, nitro, cyano, $-NR^9R^{9a}$, $-OR^9$, $-S(O)_nR^{12}$, $-COR^9$, $-CO_2R^9$, $-C(O)NR^9R^{9a}$, $-NR^9C(O)R^{9a}$, and $-C(NOR^9)R^{9a}$;

$R^{12}$ is $C_1-C_4$ alkyl;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl, 2,3-dihydrobenzofuranyl or 2,3-dihydrobenzothienyl;

n is independently at each occurrence 0, 1 or 2; and
m is independently at each occurrence 0–6.

2. A compound of formula I:

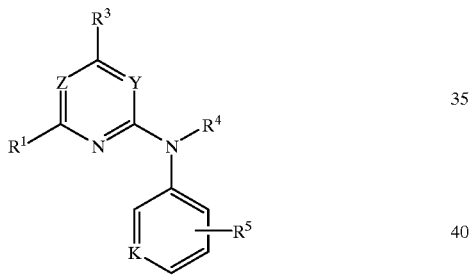

(I)

or a pharmaceutically acceptable salt or pro-drug form thereof, wherein:

Y is $CR^2$ or N;
Z is CH or N;
K is $CR^5$ or N;
$R^1$ is $C_1-C_4$ alkyl, $C_2-C_4$ alkenyl, $C_2-C_4$ alkynyl, chloro, fluoro, cyano, or trifluoromethyl;
$R^2$ taken together with $R^4$ is $-E-F-$, where E and F are independently $CR^9$ and $CR^{9a}$; or $R^2$ taken together with $R^4$ is $-A=D-$, where A and D are each independently CH, $CR^{10}$ or N; provided that $-A=D-$ may not be $-CH=N-$ or $-CR^{10}=N-$ oriented in such a way as to form a pyrazole ring, but may be $-CH=N-$ or $-CR^{10}=N-$ oriented in such a way as to form an imidazole ring; or $R^2$ taken together with $R^4$ is $-A-D-$ where A is $NR^9$ and D is C=O oriented in such a way as to form an imidazolone;
$R^3$ is phenyl which is substituted on 1–4 ring carbons of the phenyl with $R^8$, napthyl which is substituted on 1–4 ring carbons of the napthyl with $R^8$, pyridinyl which is substituted on 1–4 ring carbons of the pyridine with $R^8$ or pyrimidinyl substituted on 1–4 ring carbons of the pyrimidine with $R^8$;

$R^4$ is $C_1-C_4$ alkyl, allyl, or propargyl, where $C_1-C_4$ alkyl is optionally substituted with $C_3-C_6$ cycloalkyl, OH, $-OR^9$, $-S(O)_nR^9$ or $-CO_2R^9$;

$R^5$ represents 1–4 substituents on ring carbons each of which may be independently $C_1-C_{10}$ alkyl, $C_2-C_{10}$ alkenyl, $C_2-C_{10}$ alkynyl, $C_3-C_6$ cycloalkyl, $C_4-C_{10}$ cycloalkylalkyl, halo, nitro, cyano, $-NR^6R^7$, $-OR^7$, $-COR^7$, $-C(O)NR^6R^7$, $-C(NOR^9)R^7$, or $-S(O)_nR^7$, where $C_1-C_{10}$ alkyl, $C_2-C_{10}$ alkenyl, $C_2-C_{10}$ alkynyl, $C_3-C_6$ cycloalkyl and $C_4-C_{10}$ cycloalkylalkyl are optionally substituted with 1 to 3 substituents independently selected from the group consisting of halo, nitro, cyano, $-NR^6R^7$, $-OR^7$, $-COR^7$, $-C(O)NR^6R^7$, $-S(O)_nR^7$, and $-C(NOR^9)R^7$ and two $R^5$ moieties taken together may comprise $-CR^9R^{9a}CR^9R^{9a}O-$, $-CR^9R^{9a}CR^9R^{9a}CR^9R^{9a}-$, or $-CR^9=CR^{9a}O-$;

$R^6$ and $R^7$ are independently at each occurrence selected from the group consisting of H, $C_1-C_6$ alkyl, $C_3-C_6$ cycloalkyl, $-(CH_2)_m$-phenyl, and $-(CH_2)_m$-heteroaryl; all optionally substituted with 1–3 $R^{11}$'s;

$R^8$ is independently at each occurrence selected from the group consisting of $C_1-C_6$ alkyl, $C_2-C_6$ alkenyl, $C_2-C_6$ alkynyl, $C_3-C_6$ cycloalkyl, $C_4-C_{10}$ cycloalkylalkyl, phenyl, heteroaryl, halo, nitro, cyano, $-NR^6R^7$, $-OR^7$, $-COR^7$, $-CO_2R^7$, $-C(O)NR^6R^7$, $-OC(O)NR^6R^7$, $-NR^9C(O)NR^6R^7$, $-NR^6C(O)R^7$, $-C(NOR^9)R^7$, $-S(O)_nR^7$, $-NR^9SO_2R^7$, and $-SO_2NR^6R^7$, and where $C_1-C_6$ alkyl, $C_2-C_6$ alkenyl, $C_2-C_6$ alkynyl, $C_3-C_6$ cycloalkyl, $C_4-C_{10}$ cycloalkylalkyl, and phenyl are optionally substituted with 1 to 3 substituents independently selected from the group consisting of halo, nitro, cyano, $-NR^6R^7$, $-OR^7$, $-COR^7$, $-C(O)NR^6R^7$, $-S(O)_nR^7$, $-C(NOR^9)R^7$, $-NR^9SO_2R^7$, and $-SO_2NR^6R^7$; provided that when $R^3$ is pyridinyl, at least one $R^8$ is other than methyl; further provided that when $R^3$ is phenyl, at least one $R^8$ is other than unsubstituted phenyl;

$R^9$ and $R^{9a}$ is H or $C_1-C_4$ alkyl;

$R^{10}$ is $C_1-C_4$ alkyl, halo, nitro, cyano, $-NR^9R^{9a}$, $-OR^{12}$, or $-S(O)_nR^{12}$;

$R^{11}$ is independently at each occurrence selected from the group consisting of $C_1-C_3$ alkyl, halo, nitro, cyano, $-NR^9R^{9a}$, $-OR^9$ $-S(O)_nR^{12}$, $-COR^9$, $-CO_2R^9$, $-C(O)NR^9R^{9a}$, $-NR^9C(O)R^{9a}$, and $-C(NOR^9)R^{9a}$;

$R^{12}$ is $C_1-C_4$ alkyl;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl, 2,3-dihydrobenzofuranyl or 2,3-dihydrobenzothienyl;

n is independently at each occurrence 0, 1 or 2; and
m is independently at each occurrence 0–6;
with the provisos that:
(1) when $R^4$ is $C_1-C_4$ alkyl and Y is N, then Z is N;
(2) when $R^3$ is phenyl, Y is N, and Z is CH, at least one $R^8$ is other than dimethylamino or $-NCH_3C(O)CH_3$;
(3) when Z and K are CH, $R^5$ is $-OR^7$, and $R^7$ is $CH_2R^{11}$, then $R^{11}$ is not $CO_2R^9$; and
(4) when Y and Z are both N, K is CH, and $R^3$ is phenyl, then R1 is not chloro or fluoro.

3. A compound of claim 2 or a stereoisomer or pharmaceutically acceptable salt form thereof, wherein:

K is $CR^5$;
Y is N;
Z is CH or N;
$R^1$ is methyl;
$R^3$ is a phenyl moiety substituted with 1–3 substituents independently selected from the group consisting of: halo, methoxy, nitro, trifluoromethyl, methyl, amino, methylamino, dimethylamino, cyano, 4-tetrazolyl, carboxy, methylthio, methylsulfonyl, dichloro;
$R^4$ is ethyl;
$R^5$ is selected from the group consisting of $C_{1-4}$ alkyl, $C_{1-4}$ alkoxy, halo, acetyl, dimethylamino, cyano, methylthio, methylsulfonyl.

4. A compound of claim 2 or a stereoisomer or pharmaceutically acceptable salt form thereof, wherein:
K is $CR^5$;
Y is $CR^2$;
Z is CH or N;
$R^1$ is methyl;
$R^2$ taken together with $R^4$ is —A=D—, where A and D are each CMe or N oriented in such a way as to form an imidazole or a triazole ring, or A is $NR^9$ and D is C=O oriented in such a way as to form an imidazolone;
$R^3$ is an phenyl moiety substituted with 1–3 substituents independently selected from the group consisting of trifluoromethyl, methyl, and chloro; and
$R^5$ is selected from the group consisting of $C_{1-4}$ alkyl, $C_{1-4}$ alkoxy, halo, acetyl, dimethylamino, cyano, methylthio, and methylsulfonyl.

5. A compound of claim 2 selected from the group consisting of:
N-(2-Bromo-(1-methylethyl)phenyl)-N-ethyl-4-(2-chlorophenyl)-6-methyl-2-pyrimidineamine;
N-(2-Bromo-4,6-dimethoxyphenyl)-N-ethyl-4-(2-(trifluoromethy)phenyl)-6-methyl-2-pyrimidineamine;
N-(2-Bromo-4-(1-methylethyl)phenyl)-N-ethyl-4-(2-(trifluoromethyl)phenyl)-6-methyl-2-pyrimidineamine;
N-(2-Bromo-4-dimethylamino-6-methoxyphenyl)-N-ethyl-4-(2-(trifluoromethyl)phenyl)-6-methyl-2-pyrimidineamine;
N-(2-Bromo-4-(1-methylethyl))-N-ethyl-4-(3-(trifluoromethyl)phenyl)-6-methyl-2-pyrimidineamine;
N-(2-Bromo-4,6-dimethoxyphenyl)-N-ethyl-4-(2-chlorophenyl)-6-methyl-2-pyrimidineamine;
N-[2-Bromo-4-(1-methylethyl)phenyl]-N-ethyl-4-(2-nitrophenyl)-6-methyl-2-pyrimidineamine;
N-2,4-Dibromophenyl)-N-ethyl-4-[2-(trifluoromethyl)phenyl]-6-methyl-2-pyrimidineamine;
N-(4-Acetyl-2-bromophenyl)-N-ethyl-4-[2-(trifluoromethyl)phenyl]-6-methyl-2-pyrimidineamine;
N-[2-Bromo-4-(1-methylethyl)phenyl]-N-ethyl-4-(2-cyanophenyl)-6-methyl-2-pyrimidineamine;
N-(2-Bromo-4-methylthiophenyl)-N-ethyl-4-[2-(trifluoromethyl)phenyl]-6-methyl-2-pyrimidineamine;
N-(2-Bromo-4-methylsulfonylphenyl)-N-ethyl-4-[2-(trifluoromethyl)phenyl]-6-methyl-2-pyrimidineamine;
N-[2-Bromo-4-(1-methylethyl)phenyl]-N-ethyl-4-(2,4,6-trimethylphenyl)-6-methyl-2-pyrimidineamine;
N-(2,4-Dibromophenyl)-N-ethyl-4-(2-methylthiophenyl)-6-methyl-2-pyrimidineamine;
N-(2-Bromo-4-(1-methylethyl)phenyl)-N-ethyl-4-(2-(trifluoromethyl)phenyl)-6-methyl-1,3,5-triazine-2-amine;
N-(4-dimethylamino-2-(trifluoromethyl)phenyl)-N-ethyl-4-(2-(trifluoromethyl)phenyl)-6-methyl-1,3,5-triazine-2-amine;
9-(2-Bromo-4,-isopropylphenyl)-2-methyl-6-(2-trifluoromethyl)phenyl)-8-azapurine and
N-(2-Bromo-4-(1-methylethyl)phenyl)-N-ethyl-4-(2-methylphenyl)-6-methyl-2-pyrimidineamine; and
N-(2-Bromo-4-)-(1-methylethyl)phenyl)-N-ethyl-4-(2,6-dichlorophenyl)-6-methyl-2-pyrimidineamine.

6. A pharmaceutical composition comprising the compound of claim 2 and a pharmaceutically acceptable carrier.

7. A method of treating affective disorder, anxiety or depression in mammals, comprising: administering to the mammal a therapeutically effective amount of a compound of formula claim 2.

* * * * *